United States Patent
McArthur et al.

(10) Patent No.: US 10,470,793 B2
(45) Date of Patent: Nov. 12, 2019

(54) DEVICES FOR ROTATING MEDICAL INSTRUMENTS AND RELATED SYSTEMS AND METHODS

(71) Applicant: Merit Medical Systems, Inc., South Jordan, UT (US)

(72) Inventors: Gregory R. McArthur, Sandy, UT (US); Ken Sykes, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 215 days.

(21) Appl. No.: 15/277,473

(22) Filed: Sep. 27, 2016

(65) Prior Publication Data

US 2017/0087348 A1 Mar. 30, 2017

Related U.S. Application Data

(60) Provisional application No. 62/234,386, filed on Sep. 29, 2015, provisional application No. 62/341,164, filed on May 25, 2016.

(51) Int. Cl.
| | |
|---|---|
| *A61B 17/00* | (2006.01) |
| *A61B 17/3207* | (2006.01) |
| *A61M 39/06* | (2006.01) |
| *A61B 17/22* | (2006.01) |

(52) U.S. Cl.
CPC .......... *A61B 17/3207* (2013.01); *A61B 17/22* (2013.01); *A61M 39/0613* (2013.01); *A61B 2017/00367* (2013.01); *A61M 2039/0626* (2013.01)

(58) Field of Classification Search
CPC . A61B 17/1624; A61B 17/17; A61B 17/1626; A61B 17/1697; A61B 17/320758; A61B 2017/00469; A61B 2017/00367; A61B 2017/320024; A61B 2017/320028; A61B 2017/230032; A61M 2025/09116; A61M 25/01; B25B 15/04; B25B 15/06; B25B 17/00; Y10T 408/65; Y10T 74/18752; Y10T 74/18576
See application file for complete search history.

(56) References Cited

U.S. PATENT DOCUMENTS

| 532,145 A | * | 1/1895 | Defatsch | B25B 15/06 |
| | | | | 74/127 |
| 3,049,018 A | * | 8/1962 | Lusskin | A61B 17/1624 |
| | | | | 15/26 |
| 4,524,650 A | * | 6/1985 | Marks | B25B 17/00 |
| | | | | 173/170 |

(Continued)

OTHER PUBLICATIONS

SPINR Product Brochure, Right acquired by Merit Medical Systems, Inc., Jul. 2015.

*Primary Examiner* — Christopher L Templeton
(74) *Attorney, Agent, or Firm* — Stoel Rives LLP

(57) ABSTRACT

Medical devices for rotating an elongate medical instrument can be used to remove, break up, clear, and/or eliminate obstructions within a lumen. Some medical devices for rotating an elongate medical instrument may include a coupling member for coupling the medical device to a secondary medical device. Some medical devices may include a flared distal region and some medical devices may include an elongate housing that is disposed around a portion of the distal region.

14 Claims, 20 Drawing Sheets

(56) References Cited

U.S. PATENT DOCUMENTS

| | | | | |
|---|---|---|---|---|
| 5,213,015 A * | 5/1993 | Disston, Jr. | ............... | B25B 9/00 |
| | | | | 279/52 |
| 8,845,621 B2 | 9/2014 | Fojtik | | |
| 2008/0277445 A1* | 11/2008 | Zergiebel | ............. | A61B 17/064 |
| | | | | 227/132 |
| 2012/0239008 A1* | 9/2012 | Fojtik | .............. | A61B 17/32075 |
| | | | | 606/1 |
| 2014/0142594 A1 | 5/2014 | Fojtik | | |
| 2015/0305765 A1* | 10/2015 | Fojtik | ............. | A61B 17/32002 |
| | | | | 606/113 |

\* cited by examiner

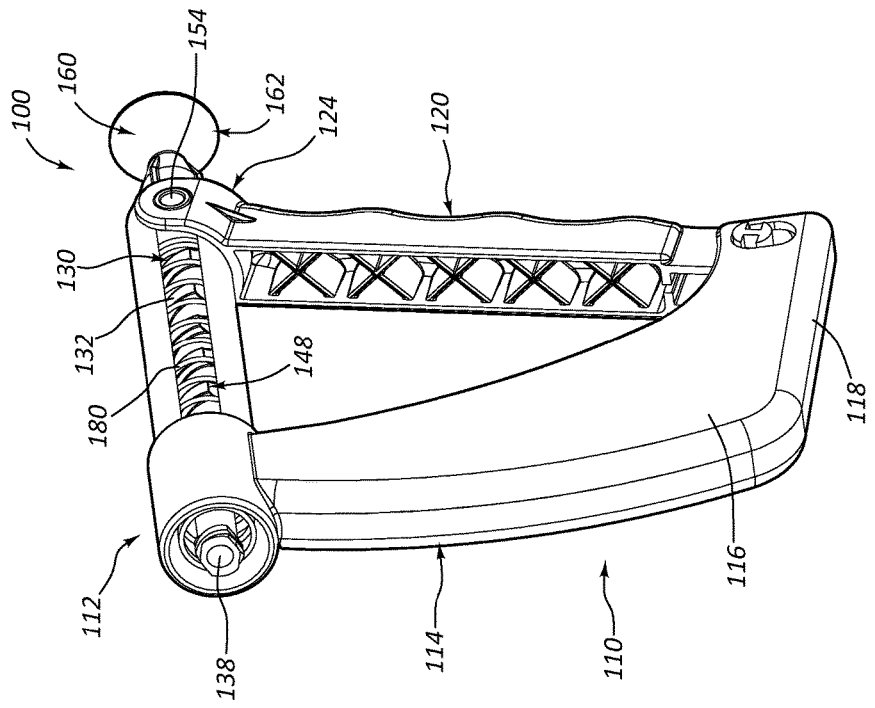
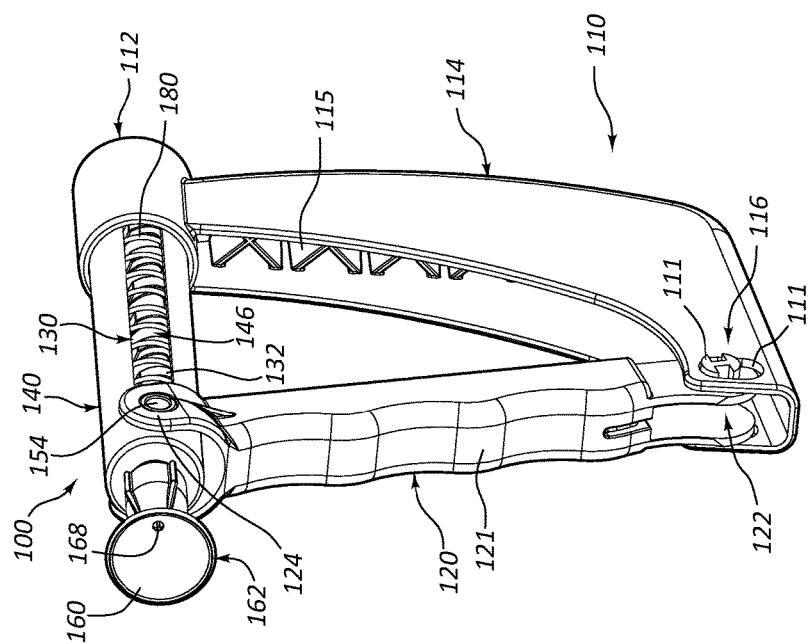

DEVICES FOR ROTATING MEDICAL INSTRUMENTS AND RELATED SYSTEMS AND METHODS

RELATED APPLICATIONS

This application claims priority to U.S. Provisional Application No. 62/234,386, filed on Sep. 29, 2015 and titled, "Devices for Rotating Medical Instruments and Related Systems and Methods," and U.S. Provisional Application No. 62/341,164, filed on May 25, 2016 and titled, "Devices for Rotating Medical Instruments and Related Systems and Methods," both of which are hereby incorporated by reference in their entireties.

TECHNICAL FIELD

This application is generally related to the field of medical devices. For example, some embodiments disclosed herein relate to medical devices for rotating one or more medical instruments. Some of the medical devices for rotating one or more medical instruments may be used to remove, break up, clear, bypass, and/or eliminate an obstruction within a lumen.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1B is a perspective view of the medical device of FIG. 1A in an assembled configuration.

FIG. 1C is an alternative perspective view of the medical device of FIG. 1A in an assembled configuration.

DETAILED DESCRIPTION

Figure 1A:
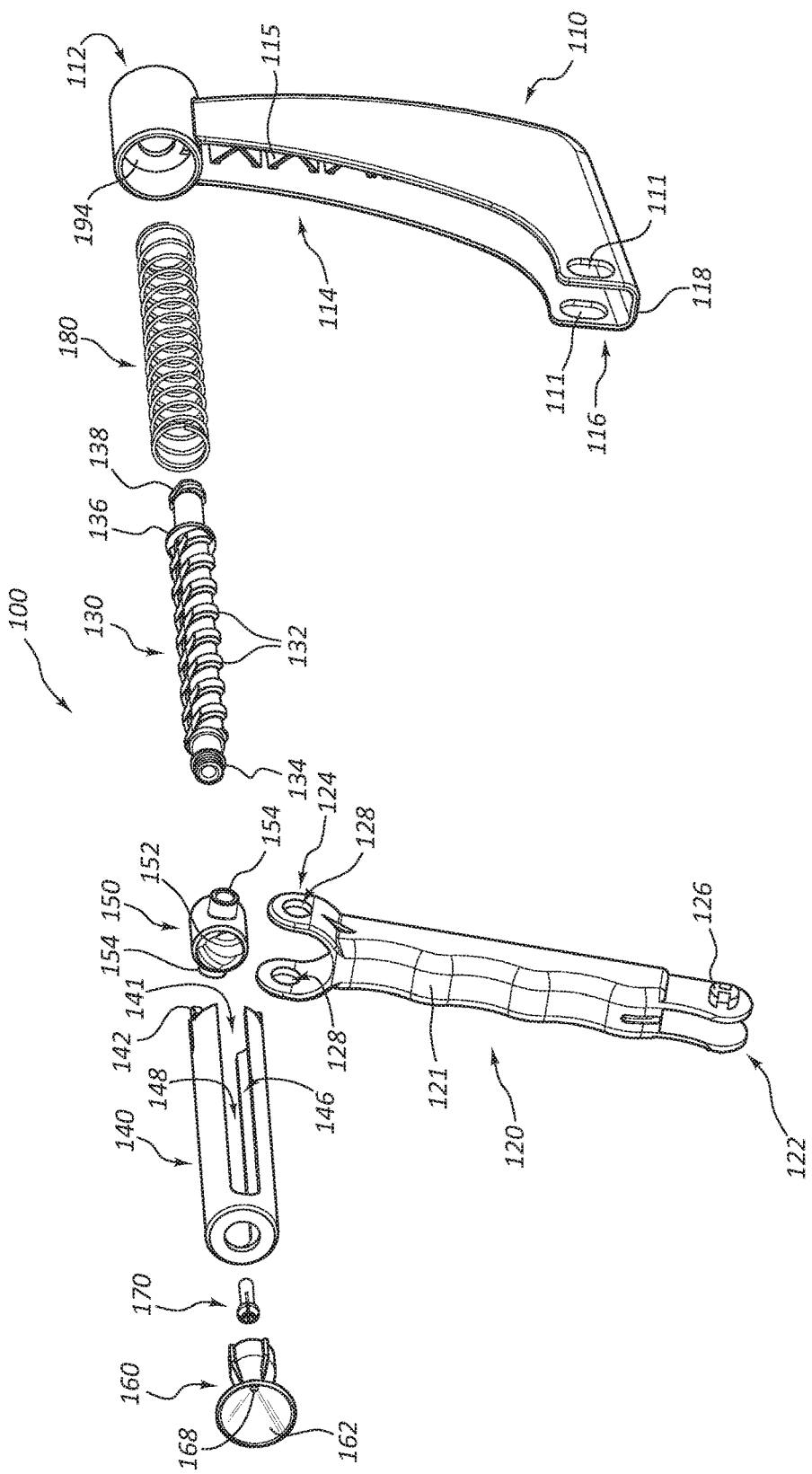
FIG. 1A is an exploded perspective view of a medical device for rotating an elongate medical instrument.

An obstruction within a body lumen can present numerous challenges and/or risks to a patient or a medical practitioner. For example, an obstruction within the vasculature, such as a thrombus or plaque build-up (e.g., atherosclerosis), may disturb blood flow, thereby causing harm or death to an individual. Further, an obstruction within a body lumen may make it difficult for a practitioner to access a region of the patient that is disposed on the other side of the obstruction. Accordingly, methods and devices for removing or bypassing an obstruction within a lumen are needed to improve patient health and simplify patient care.

Medical devices, such as those disclosed herein, may be used to help remove, break up, clear, bypass, and/or eliminate an obstruction within a lumen. For example, in some embodiments, a medical device may be coupled to and rotate an elongate medical instrument (e.g., an elongate wire or tube, including embodiments wherein a secondary tool such as a drill bit or a cutting element is disposed adjacent a distal end of the elongate wire or tube) to break up an obstruction within a lumen. In this manner, the medical device may function as a macerator that reduces a solid obstruction to smaller pieces. In some circumstances or embodiments, a medical device may rotate a wire, such as a guidewire, within a body lumen to identify or follow a path of lesser resistance through a blockage, narrowing, or obstruction. In other words, a practitioner may use the medical device to rotate a wire within a body lumen to probe a plurality of locations to find or identify a path of lesser resistance through or around an obstruction. The wire may then be used to facilitate advancement of one or more other materials or implements through or around the obstruction.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. Components that are "directly coupled" to each other are in direct contact with each other or are separated from each other only by a fastener of any suitable variety.

The terms "proximal" and "distal" are opposite directional terms. For example, the distal end of a device or component is the end of the device or component that is furthest from the practitioner during ordinary use. The proximal end refers to the opposite end or the end nearest the practitioner during ordinary use. The terms "upper," "lower," "top," "bottom," "vertical," "upward," and "downward" are used with reference to the orientation of the medical device depicted in FIG. 1F. A line is "substantially perpendicular" to another line if the lines intersect within 15 degrees of a right angle.

The term "resilient" refers to a component, device, or object having a particular shape that can then be elastically deformed into a different shape, but that may return to the original shape when unconstrained. For example, a resilient arm may extend along the longitudinal direction of a coupling member and, in use, the resilient arm may then be constrained (i.e., temporarily engaged with and/or disposed over a portion of a secondary medical device) to elastically deform it into a second shape (i.e., displaced radially outward due to interaction with the portion of the secondary medical device), then unconstrained (i.e., removed from engagement with the secondary medical device) such that the resilient arm returns to its first shape or substantially returns to its first shape.

Figure 1E:
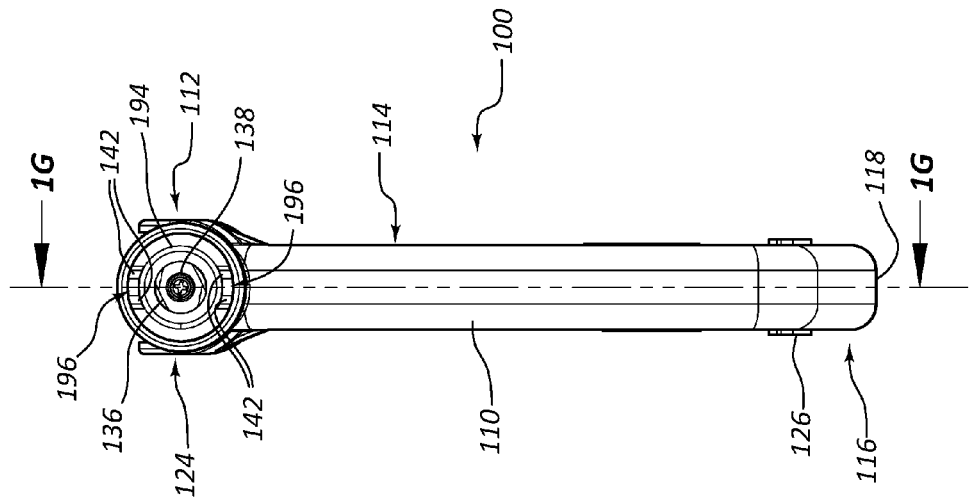
FIG. 1E is a back view of the medical device of FIG. 1A.
Figure 1D:
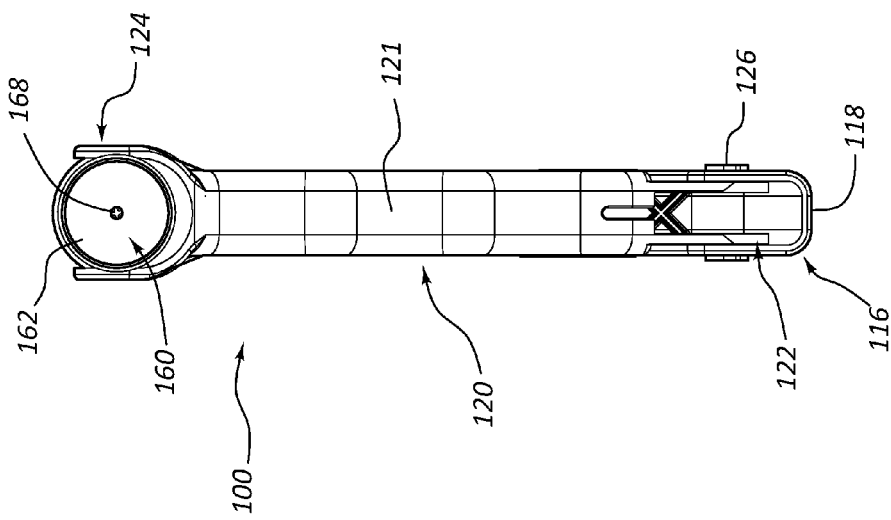
FIG. 1D is a front view of the medical device of FIG. 1A.
Figure 1F:
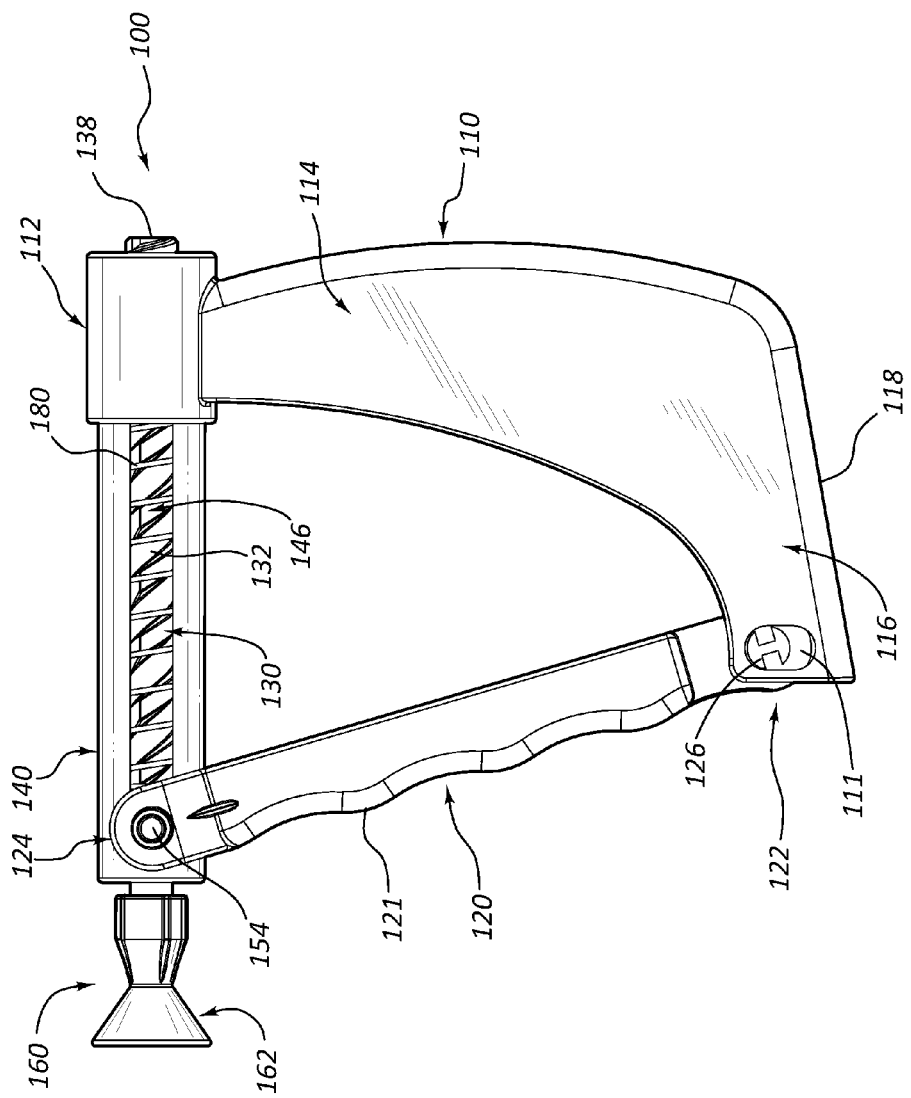
FIG. 1F is a side view of the medical device of FIG. 1A.
Figure 1G:
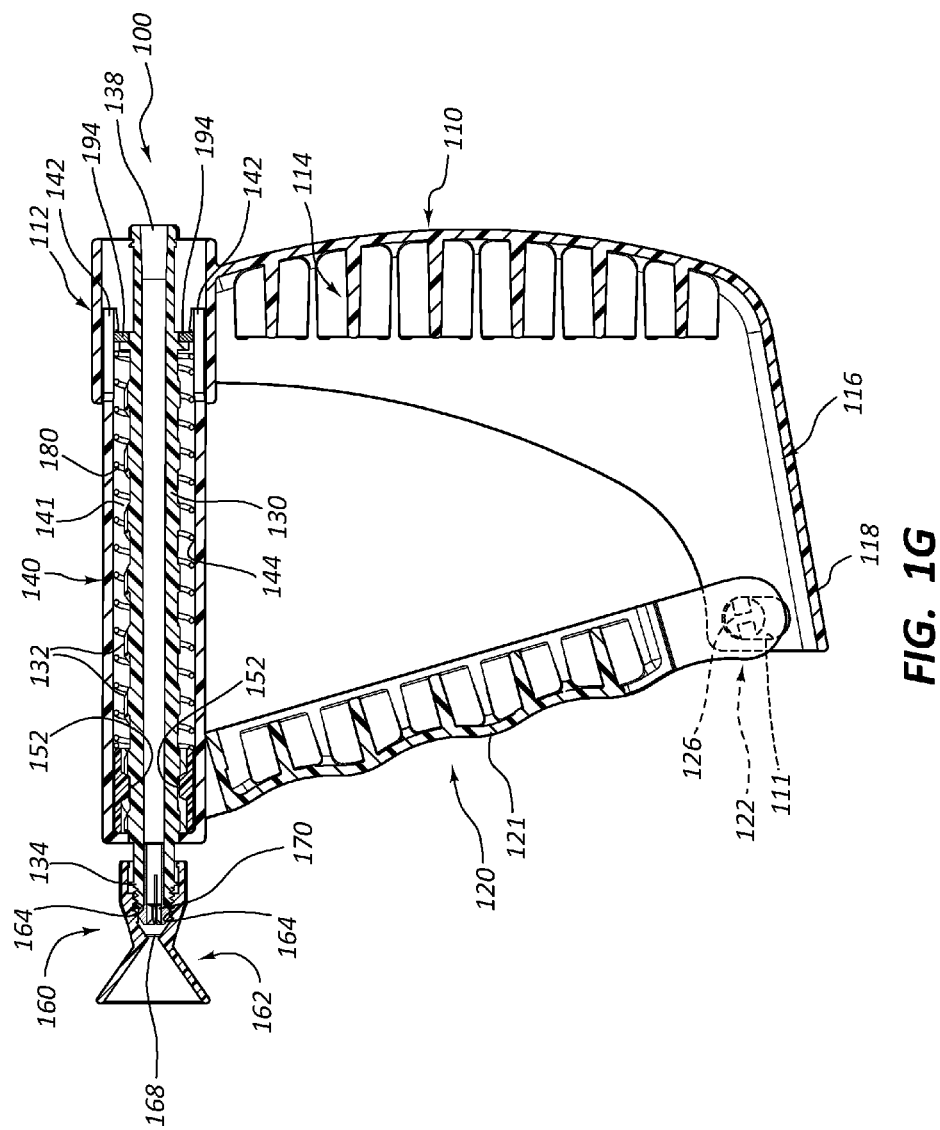
FIG. 1G is a cross-sectional side view of the medical device of FIG. 1A.

FIGS. 1A-1G provide alternative views of a medical device 100 that is configured to rotate an elongate medical instrument. (The elongate medical instrument is not shown in FIGS. 1A-1G.) More particularly, FIG. 1A provides an exploded perspective view of the medical device 100. FIGS. 1B and 1C provide alternative perspective views of the medical device 100 in an assembled configuration. FIGS. 1D, 1E, and 1F provide front, back, and side views, respectively, of the assembled medical device 100. FIG. 1G provides a cross-sectional side view of the assembled medical device 100.

With reference to FIGS. 1A-1G, the medical device 100 may include one or more of the following elements: a handle 110, an actuator 120, an elongate shaft 130, a housing 140, a translatable member 150, a distal endpiece 160, a gripping member 170, and a biasing member 180.

As shown in FIGS. 1A-1G, the handle 110 may be configured for contact with a region of a hand disposed between a thumb and an index finger (e.g., a palm of the hand). In some embodiments, the handle 110 is generally proximally positioned relative to other components of the medical device 100.

The handle 110 may include an upper portion 112, an intermediate portion 114, and a lower portion 116. In some embodiments, such as the embodiment depicted in FIGS. 1A-1G, the upper portion 112, the intermediate portion 114, and the lower portion 116 are integrally formed.

The upper portion 112 of the handle 110 may be coupled to one or more of the housing 140 and the elongate shaft 130. For example, in the depicted embodiment, the upper portion 112 of the handle 110 is cylindrically shaped with a surface 194 that extends radially inward from the cylindrical outer surface of the upper portion 112. The surface 194 may include one or more apertures 196. When in an assembled configuration, one or more catches 142 disposed adjacent a proximal end of the housing 140 may extend through the one or more apertures 196 to securely engage the surface 194. In other or further embodiments, the elongate shaft may be rotatably coupled directly to the handle.

The intermediate portion 114 of the handle 110 may extend generally downward from the upper portion 112 of the handle 110. As shown in the depicted embodiment, the intermediate portion 114 may comprise one or more reinforcing elements 115 to strengthen and/or stiffen the handle 110. In some embodiments, the entire handle 110 is substantially rigid. Thus, in some embodiments, the handle 110 does not deflect when the device is in use.

The lower portion 116 of the handle 110 may extend both downward and distally from the intermediate portion 114 of the handle 110. In some embodiments, the handle may lack a lower portion that extends distally from the intermediate portion. Stated differently, in some embodiments, both the intermediate and lower portions of the handle extend generally downward from the upper portion without extending in a distal direction. In some embodiments, as depicted in FIGS. 1A-1G, the handle 110 may be wider toward the bottom of the handle 110 than toward the top (or an intermediate portion) of the handle 110. Stated differently, the width of the handle 110 may increase toward the bottom of the handle 110. One of ordinary skill in the art, with the benefit of this disclosure, will recognize that the handle 110 may be shaped in a variety of ways without departing from the scope of this disclosure.

The lower portion 116 of the handle 110 may include a bottom surface 118. When the medical device 100 is in an assembled configuration and the elongate shaft 130 is parallel to the ground, the bottom surface 118 of the handle 110 may be parallel to or form an angle of less than or equal to 30°, 20°, and/or 10° relative to the ground. In some embodiments, the bottom surface 118 of the handle 110 does not deflect toward the elongate shaft 130 when the medical device 100 is in use, such as when the actuator 120 (further detailed below) is displaced toward the handle 110. Stated differently, in some embodiments, the lower portion 116 of the handle 110 may not be displaced without causing simultaneous displacement of an upper portion 112 of the handle 110. In some embodiments, the lower portion 116 of the handle 110 includes an elongate slot 111, which is discussed in greater detail below.

As noted above, the medical device 100 may include an actuator 120. The actuator 120 may include a first end 122 and a second end 124. In some embodiments, the actuator 120 is coupled to the handle 110 adjacent the first end 122. More particularly, the first end 122 of the actuator 120 may be coupled to a lower portion 116 of the handle 110. In some embodiments, the first end 122 of the actuator 120 is coupled to the lower portion 116 of the handle via a protrusion 126 that extends through a slot 111 of the handle 110. The slot 111 may be elongate in shape and orientated such that the longitudinal axis of the slot 111 is perpendicular or substantially perpendicular to the longitudinal axis of the elongate shaft 130. The actuator 120 may also be coupled to a translatable member 150 adjacent the second end 124. For instance, in the depicted embodiment, the actuator 120 includes a U-shaped region adjacent the second end 124. Stated differently, the second end 124 may form a U-shaped valley. Openings 128 may be disposed on opposite sides of the U-shaped valley. The openings 128 may be configured for coupling to protrusions 154 of the translatable member 150. Thus, the actuator 120 may couple to and extend between the translatable member 150 and the handle 110. The actuator 120 may also include a distal surface 121 that is contoured to receive one or more fingers of a practitioner. As described in further detail in connection with FIGS. 3A-3C, displacement of the actuator 120 may cause both displacement of the translatable member 150 along the elongate shaft 130 and rotation of the elongate shaft 130 about its longitudinal axis. In some embodiments, displacement of the actuator 120 causes more linear displacement of the second end 124 of the actuator relative to the handle 110 than linear displacement of the first end 122 of the actuator 120 relative to the handle 110.

The medical device 100 may further include an elongate shaft 130 that extends distally from the handle 110. The elongate shaft 130 may include one or more sets of threads. For instance, in the embodiment depicted in FIGS. 1A-1G, the elongate shaft 130 includes a first set of threads 132 and a second set of threads 134. In some embodiments, the first set of threads 132 is disposed proximal of the second set of threads 134 when the medical device 100 is in an assembled configuration. The first set of threads 132 may be configured for complementary engagement with interior threads 152 of the translatable member 150. Further, in some embodiments, the first set of threads 132 is configured to cause rotation of the elongate shaft 130 in response to displacement of the actuator 120. The number of rotations through which the elongate shaft 130 rotates as the actuator 120 is displaced may depend on the helical pitch of the threads 132. Threads 132 of relatively high pitch may cause less rotation of the elongate shaft 130 than threads of relatively low pitch. In some embodiments, the pitch of the threads 132 is uniform, while in other embodiments, the pitch of the threads 132 is variable along a length of the elongate shaft 130.

The second set of threads 134 may be configured for threaded engagement with an endpiece 160. The elongate shaft 130 may optionally include a luer connection adjacent its proximal end.

In some embodiments, the elongate shaft 130 includes one or more annular rings 136 or other protrusions that extend radially outward from the remainder of the elongate shaft 130. For instance, an annular ring 136 may be disposed proximal of the first set of threads 132 and configured for contact with the surface 194 of the upper portion 112 of the housing 140, thereby restricting proximal displacement of the elongate shaft 130 with respect to the handle 110. Distal displacement of the elongate shaft 130 may be restricted by an interaction between the elongate shaft 130 and a distal portion of the housing 140. For example, in some embodiments, a thread of (or protrusion from) the elongate shaft 130 may interact with an inner surface of the housing 140 that is disposed adjacent a distal end of the housing 140, thereby restricting distal displacement of the elongate shaft 130 relative to the handle 110. In other embodiments, the elongate shaft 130 may include a second annular ring (not shown) that is disposed distal of the first set of threads 132 and proximal of the second set of threads 134. The second annular ring may be configured to interact with an inner surface of the housing 140 that is disposed adjacent a distal end of the housing 140 to restrict distal displacement of the elongate shaft 130 relative to the handle 110. One of ordinary skill in the art with the benefit of this disclosure will recognize that protrusions other than an annular ring 136 may analogously restrict displacement of the elongate shaft 130 relative to one or more other components of the medical device 100.

When the medical device 100 is in an assembled configuration, an elongate housing 140 may at least partially house the elongate shaft 130. As shown in FIGS. 1A-1G, the housing 140 may include an inner surface that forms an interior portion 141 that extends through the housing 140. The interior portion 141 may be sized to accommodate (1) at least a portion of the elongate shaft 130, (2) at least a portion of the translatable member 150, and/or (3) the biasing member 180.

The housing 140 may protect the elongate shaft 130, such as by preventing inadvertent contact with the elongate shaft 130. In some embodiments, the housing 140 may be coupled to the handle 110 and extend distally from the handle 110. For example, in the depicted embodiment, the housing 140 includes one or more catches 142 disposed adjacent a proximal end of the housing 140. The catches 142 may be configured to extend through one or more apertures 196 of the surface 194 that extends radially inward from the outer cylindrical surface of the upper portion 112 of the handle 110. As the catches 142 are delivered through the aperture 196, the catches 142 may engage with the surface 194 to securely couple the housing 140 to the handle 110.

In some embodiments, the housing 140 may include a first slot 146 and a second slot 148 that extend longitudinally along a length of the housing 140. In some embodiments, the slots 146, 148 are disposed on opposite sides of housing 140. The slots 146, 148 may be sized and shaped to accommodate a portion of the translatable member 150, as further detailed below.

The medical device 100 may additionally or alternatively include a translatable member 150. The translatable member 150 may include interior threads 152 configured to couple to the first set of threads 132 of the elongate shaft 130. Stated differently, the translatable member 150 may be configured for threaded engagement with a plurality of exterior threads 132 of the elongate shaft 130. The translatable member 150 may further include one or more protrusions 154. The protrusions 154 may be configured to couple to a second end 124 of the actuator 120. For example, in the depicted embodiment, the protrusions 154 are configured to be securely disposed within openings 128 adjacent the second end 124 of the actuator 120. The translatable member 150 may be configured to travel longitudinally along the elongate shaft 130, thereby causing rotation of the elongate shaft 130. In the depicted embodiment, as the translatable member 150 travels longitudinally along the elongate shaft 130, the protrusions 154 travel longitudinally within the slots 146, 148 of the housing 140. For example, the translatable member 150 may travel longitudinally along the elongate shaft 130 without rotating relative to housing 140.

The translatable member 150 may be shaped in any suitable manner. For example, in the depicted embodiment, the translatable member 150 is generally cylindrical in shape with one or more protrusions 154 that extend radially outward from the cylindrical surface. In the depicted embodiment, the translatable member 150 includes interior threads 152 that are configured to engage with exterior threads 132 of the elongate shaft 130. However, in other embodiments, the translatable member may include exterior threads that are configured to engage with interior threads of the elongate shaft.

The medical device 100 may additionally or alternatively include a gripping member 170, such as a chuck or collet. In some embodiments, the gripping member 170 is at least partially disposed within a lumen 138 of the elongate shaft 130. Stated differently, the gripping member 170 may be configured to be disposed adjacent a distal end of the elongate shaft 130. In some embodiments, the gripping member 170 is coupled to the elongate shaft 130 such that rotation of the elongate shaft 130 causes rotation of the gripping member 170. Thus, in some embodiments, the gripping member 170 may be fixedly coupled to the elongate shaft 130.

The gripping member 170 may be configured to transition from an open and unconstrained configuration to a closed and constrained configuration. When in an open and unconstrained configuration, a lumen of the gripping member is sized to allow insertion of an elongate medical instrument (not shown in FIGS. 1A-1G) into the medical device 100. When the elongate medical instrument is disposed within the medical device 100, the gripping member 170 may transition from an open unconstrained configuration to a closed constrained configuration, thereby securely engaging the elongate medical instrument. For instance, by applying a radially inward force to an exterior surface of the gripping member 170, the gripping member 170 (e.g., a collet) may clamp down on and securely engage the elongate medical instrument.

The medical device 100 may additionally or alternatively include an endpiece 160 that is coupled to the distal end of the elongate shaft 130. The endpiece 160 may include a flared distal region 162 and a channel that extends through the endpiece 160. The flared distal region 162 may be configured to facilitate insertion of a portion of the elongate medical instrument into a portion of the channel that is proximal of the flared distal region 162. Stated differently, the flared distal region 162 may be sloped toward an aperture 168 that is disposed at a center of the flared distal region 162 (see FIG. 1D). In some embodiments, the endpiece 160 further comprises threads 164 that are disposed proximal of the flared distal region 162. The interior threads 164 of the endpiece 160 may be configured for threaded engagement with a distal portion of the elongate shaft 130. For instance, interior threads 164 of the endpiece 160 may be configured to threadably engage with the second set of threads 134 of the elongate shaft 130.

In some embodiments, the medical device 100 includes a biasing member 180, such as a spring. The biasing member 180 may distally bias the translatable member 150 and/or the second end 124 of the actuator 120. For instance, the biasing member 180 may be compressed between and interact with the translatable member 150 and the handle 110, thereby distally biasing the translatable member 150 and the second end 124 of the actuator 120. For example, the biasing member 180 may be compressed between a surface 194 of the upper portion of the handle 110 and the one or more protrusions 154 of the translatable member 150. In some embodiments, the biasing member 180 may be at least partially disposed within the housing 140 when the medical device 100 is in an assembled configuration.

Figure 2A:
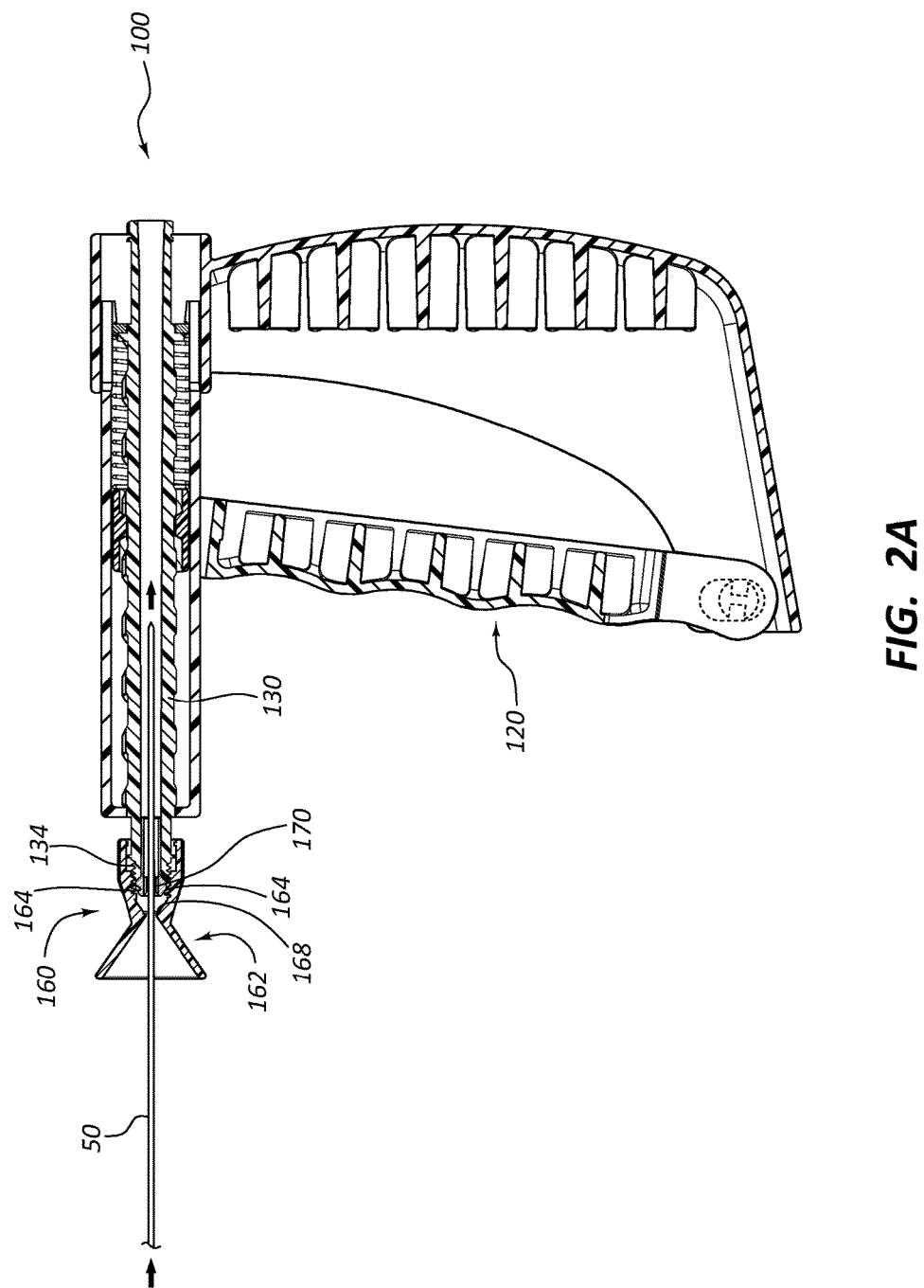
FIG. 2A is a cross-sectional side view of the medical device of FIG. 1A with an elongate medical instrument partially disposed within, but not securely coupled to, the medical device.
Figure 2B:
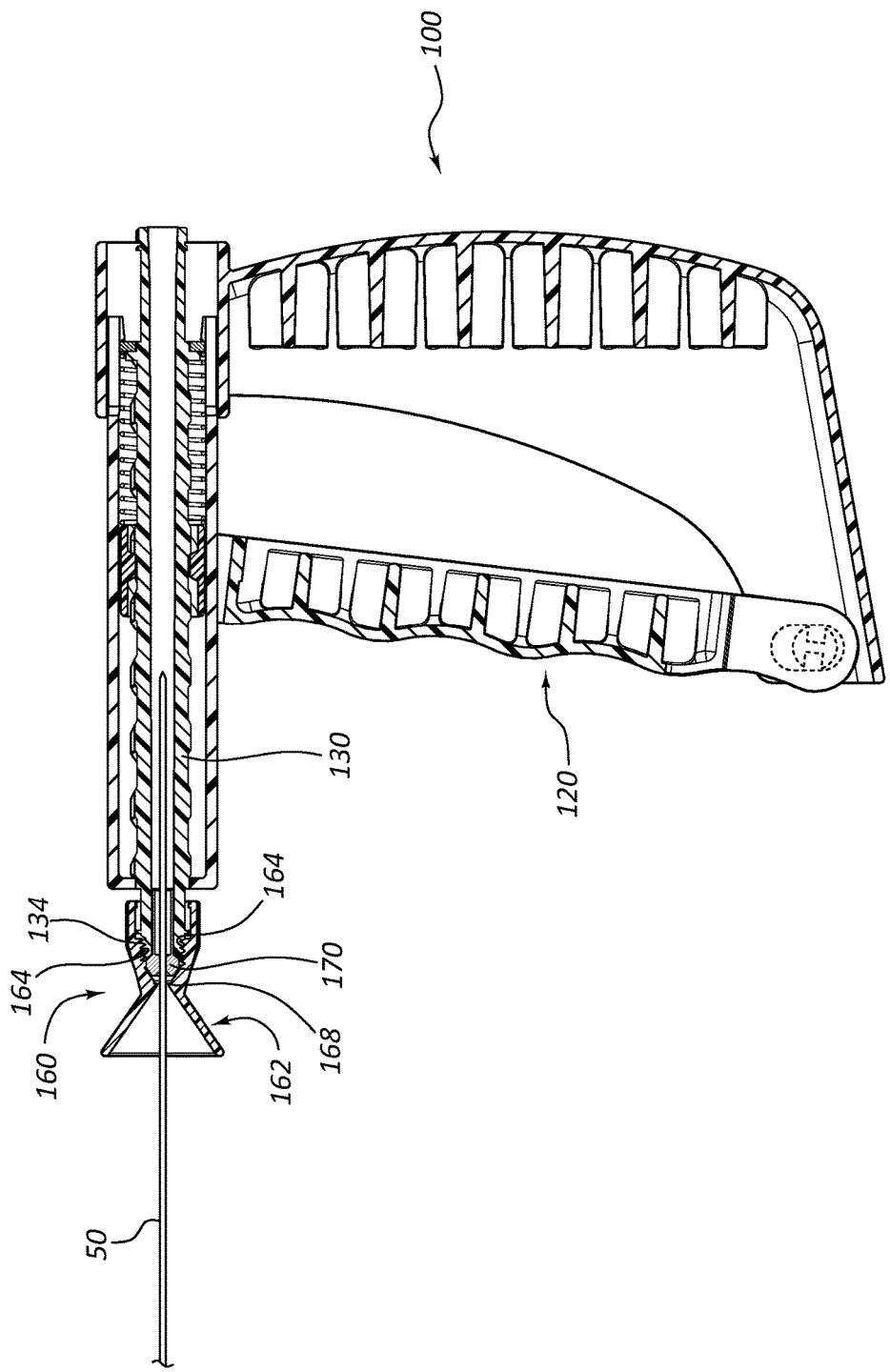
FIG. 2B is a cross-sectional side view of the medical device of FIG. 2A with an elongate medical instrument partially disposed within and securely coupled to the medical device.

FIG. 2A is a cross-sectional side view depicting the insertion of a portion of an elongate medical instrument 50 into the medical device 100. When the medical device 100 is in the configuration depicted in FIG. 2A, the elongate medical instrument 50 is not coupled to the medical device 100. FIG. 2B is a cross-sectional side view depicting the elongate medical instrument 50 and the medical device 100 in a configuration in which the elongate medical instrument 50 is coupled to the medical device 100. In FIGS. 2A-2B, the actuator 120 is shown in a partially retracted state.

As shown in FIG. 2A, a practitioner may insert a portion of an elongate medical instrument 50 into the medical device 100 by pushing the elongate medical instrument 50 through an aperture 168 disposed adjacent a distal end of the medical device 100. The elongate medical instrument 50 may be any elongate medical instrument suitable for rotation in a body lumen, such as a wire (e.g., a guidewire), a macerator, a needle, a drill bit, a trocar, or a catheter.

As the practitioner (or other person) attempts to insert the elongate medical instrument 50 into the medical device 100, the elongate medical instrument 50 may interact with the flared distal region 162 of the endpiece 160 to guide the elongate medical instrument 50 through the aperture 168 of the endpiece 160. In other words, the flared distal region 162 may provide a relatively large surface for interacting with the elongate medical instrument 50 and guide the elongate medical instrument 50 toward the aperture 168. This relatively large surface for interacting with a proximal end of the elongate medical instrument 50 may facilitate more rapid insertion of a portion of the elongate medical instrument 50 into the medical device 100. The flared distal region 162 may also decrease the dexterity needed for inserting an elongate medical instrument 50 through the aperture 168.

When the medical device 100 is in the configuration depicted in FIG. 2A, the interior threads 164 of the endpiece 160 are in partial threaded engagement with the second set of threads 134 of the elongate shaft 130. When the interior threads 164 of the endpiece 160 are partially engaged with the second set of threads 134 as shown in FIG. 2A, no (or minimal) radially compressive force is applied to the gripping member 170, thereby allowing the gripping member 170 to remain in an open uncompressed state. In this open uncompressed state, the elongate medical instrument 50 may be displaced relative to the gripping member 170.

By further rotating the endpiece 160 relative to the elongate shaft 130, the medical device 100 may transition to a configuration in which the interior threads 164 of the endpiece 160 are in full threaded engagement with the second set of threads 134 of the elongate shaft 130 (see FIG. 2B). When the interior threads 164 of the endpiece 160 are in full threaded engagement with the second set of threads 134 of the elongate shaft 130, the endpiece 160 may interact with the gripping member 170 to contract (e.g., radially compress) the gripping member 170 around the elongate medical instrument 50. Such contraction may securely couple the elongate medical instrument 50 to the medical device 100. Stated differently, the endpiece 160 may be configured to interact with the gripping member 170 such that the gripping member 170 is in a contracted state when the endpiece 160 is in full threaded engagement with the elongate shaft 130.

In other words, during a medical procedure for disrupting an obstruction within a lumen (e.g., a vascular lumen), a practitioner may obtain the medical device 100 and the elongate medical instrument 50. The practitioner may then insert a portion (e.g., a proximal portion) of the elongate medical instrument 50 into the medical device 100 and securely couple the elongate medical instrument 50 to the medical device 100. More specifically, the practitioner may insert a portion of the elongate medical instrument 50 into the aperture 168 of the medical device 100 that is disposed at a center of the flared distal region 162 of the endpiece 160. The practitioner may then engage the elongate medical instrument 50 such that the elongate medical instrument 50 is coupled to a rotatable shaft (e.g., the elongate shaft 130). For example, in some embodiments, the practitioner may rotate the endpiece 160 to fully engage the interior threads 164 of the endpiece 160 with the second set of threads 134 of the elongate shaft 130, thereby compressing the gripping member 170 around the elongate medical instrument 50 to securely engage the elongate medical instrument 50.

In some medical procedures, the practitioner may insert the elongate medical instrument 50 into a lumen (e.g., a body lumen) in which there is an obstruction. In some embodiments, insertion of the elongate medical instrument 50 into the lumen occurs prior to insertion of the elongate medical instrument 50 into the medical device 100. In other embodiments, the elongate medical instrument 50 is inserted into the lumen after the elongate medical instrument 50 has been inserted into the medical device 100. Once the elongate medical instrument 50 is disposed within the lumen and securely coupled to the medical device 100, the actuator 120 may be displaced as described in further detail below in connection with FIGS. 3A-3C, causing rotation of the elongate medical instrument 50 within the lumen. In some embodiments, the medical instrument 50 may be advanced and/or retracted within the lumen while displacing the actuator 120. Such displacement and/or rotation of the elongate medical instrument 50 may break up, clear, bypass, and/or eliminate one or more obstructions within the lumen.

Figure 3A:
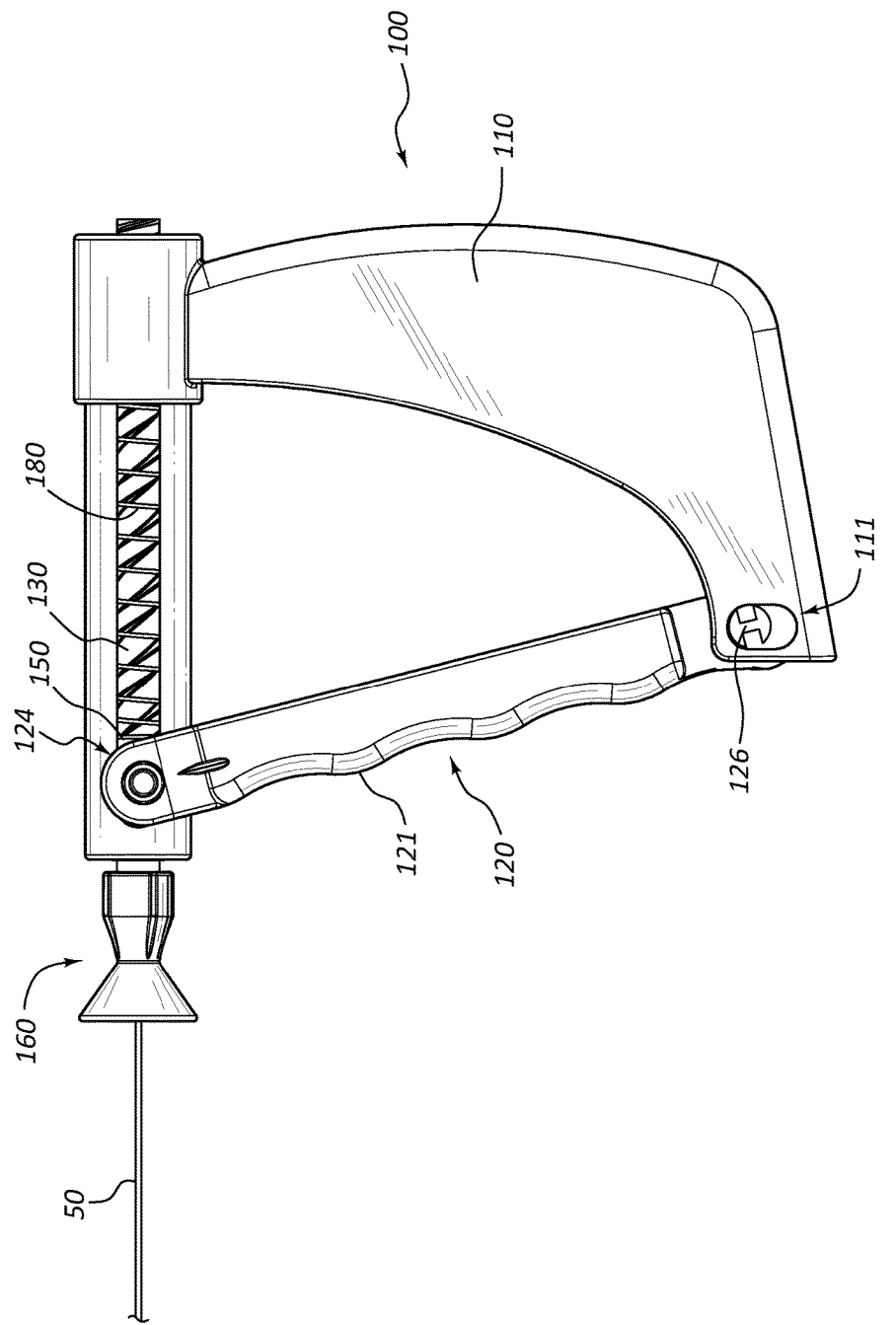
FIG. 3A is a side view of the medical device of FIG. 1A in a first state.
Figure 3B:
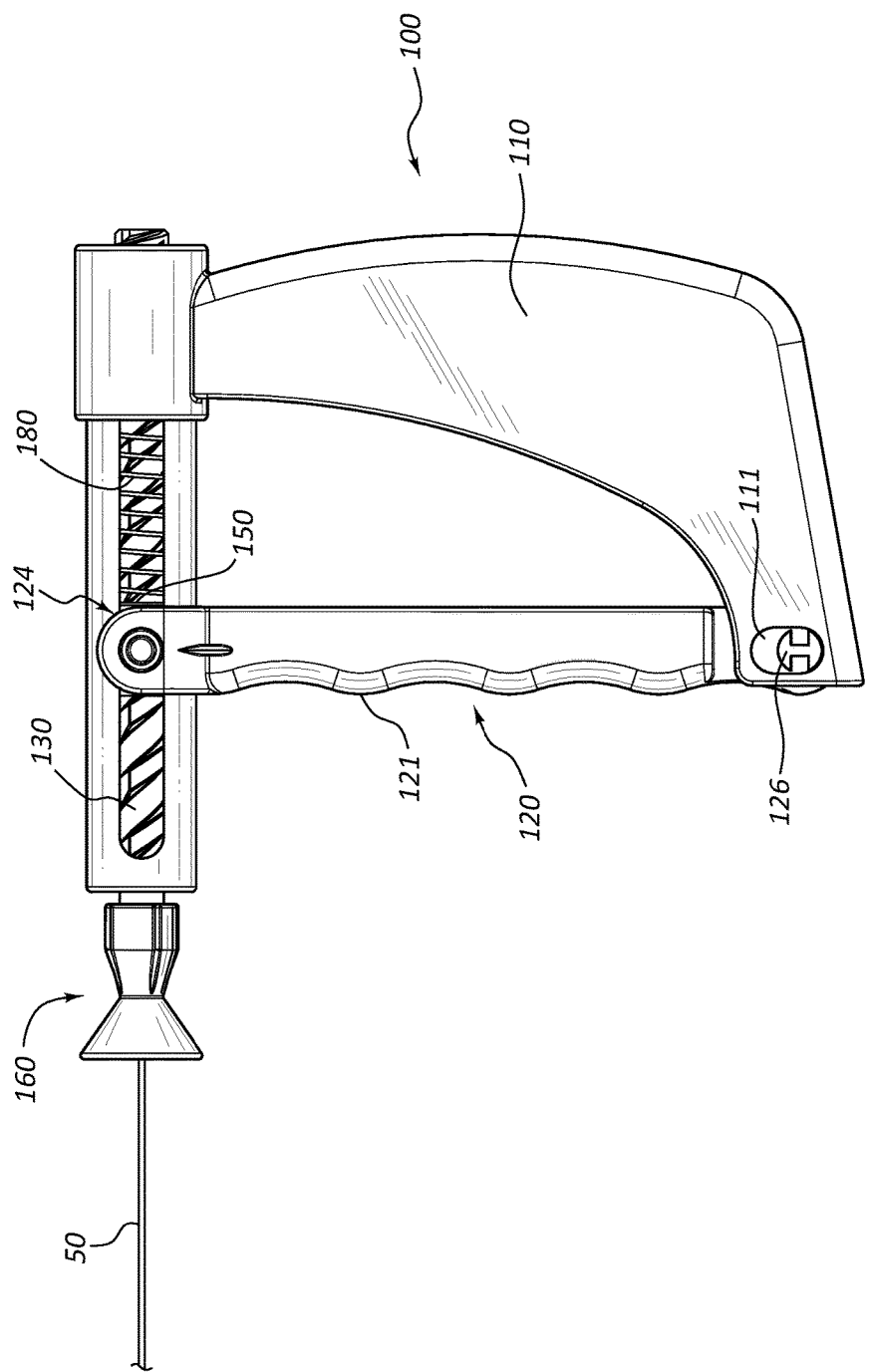
FIG. 3B is a side view of the medical device of FIG. 3A in a second state.
Figure 3C:
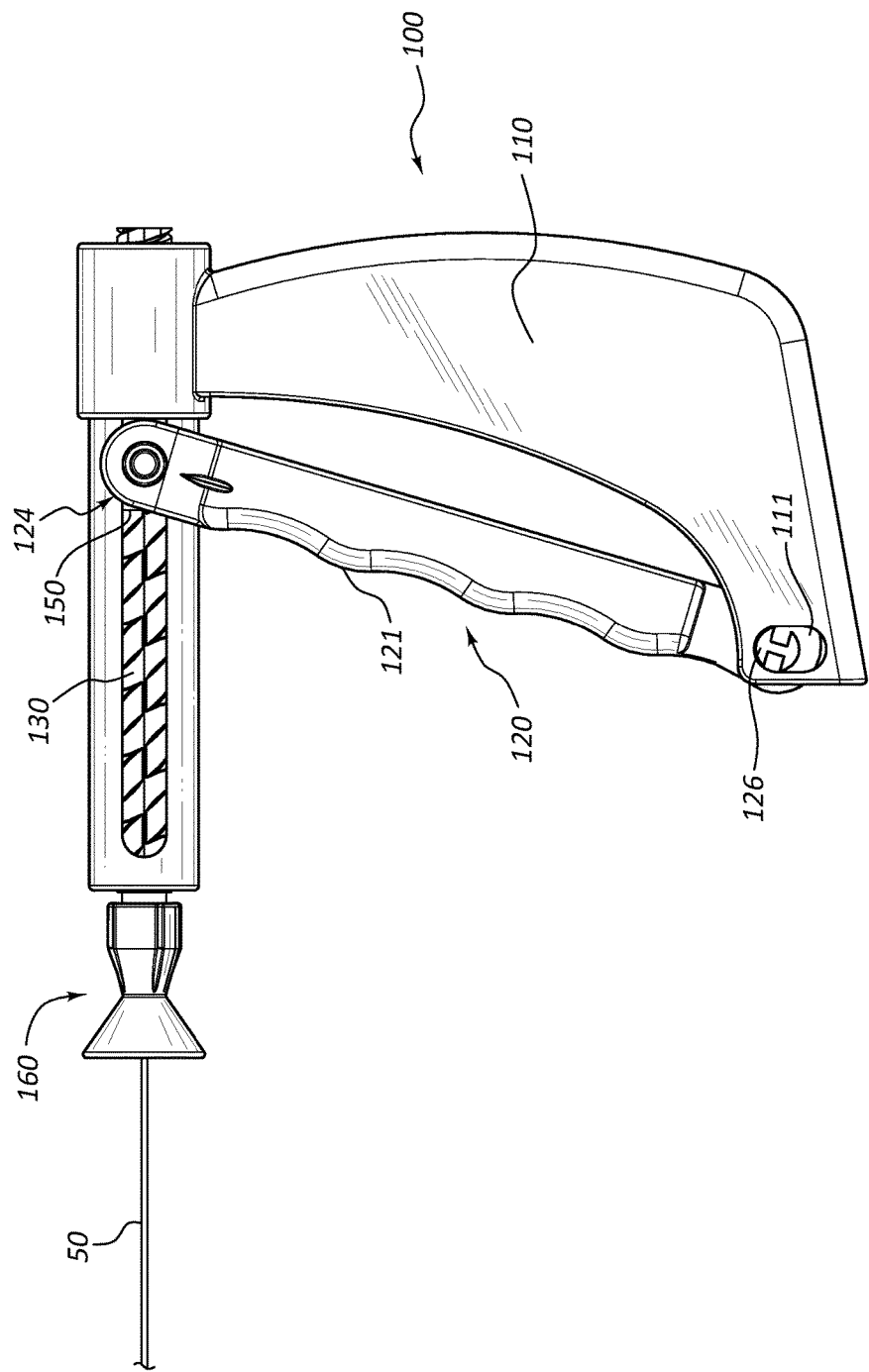
FIG. 3C is a side view of the medical device of FIG. 3A in a third state.

FIGS. 3A-3C depict the medical device 100 in three different operational states. More particularly, FIG. 3A depicts the medical device 100 in a state in which the second end 124 of the actuator 120 is disposed adjacent a distal end of the elongate shaft 130. FIG. 3B depicts the medical device 100 in a state in which the second end 124 of the actuator 120 is disposed adjacent an intermediate portion of the elongate shaft 130. And FIG. 3C depicts the medical device 100 in a state in which the second end 124 of the actuator 120 is disposed adjacent a proximal portion of the elongate shaft 130. FIGS. 3A-3C may be understood to depict sequential states of the medical device 100 during a portion of an operation sequence.

For instance, during a medical procedure in which an elongate medical instrument 50 is inserted within a lumen and coupled to (e.g., securely engaged by or fixedly engaged with) the gripping member 170 as described above in connection with FIGS. 2A and 2B, the medical device 100 may be biased to the configuration depicted in FIG. 3A in which the second end 124 of the actuator 120 is disposed adjacent a distal end of the elongate shaft 130. Such distal bias may be provided by the distal biasing member 180 (e.g., a spring), which interacts with and pushes the translatable member 150 in a distal direction. From this state, the practitioner may displace the actuator 120 relative to the threaded elongate shaft 130 (see FIGS. 3B and 3C), thereby causing (1) linear displacement of the translatable member 150 along the elongate shaft 130, (2) rotation of the elongate shaft 130, and/or (3) rotation of the elongate medical instrument 50. More particularly, proximal displacement of the second end 124 of the actuator 120 relative to the elongate shaft 130 may cause proximal displacement of the translatable member 150 relative to the elongate shaft 130. As the translatable member 150 is displaced relative to the elongate shaft 130, the interior threads 152 of the translatable member 150 may interact with the first set of exterior threads 132 of the elongate shaft 130, thereby causing rotation of the elongate shaft 130 about the longitudinal axis of the elongate shaft 130. Rotation of the elongate shaft 130 may cause rotation of the gripping member (not shown), the endpiece 160, and/or the elongate medical instrument 50. In other words, the gripping member, the endpiece 160, and/or the elongate medical instrument 50 may be coupled to the elongate shaft 130 such that rotation of the elongate shaft 130 rotates the gripping member 170, the endpiece 160, and/or an elongate medical instrument 50 that is securely held by the gripping member 170.

As the second end 124 of the actuator 120 is proximally displaced by the practitioner (e.g., by drawing one or more fingers toward the palm of the hand), the elongate shaft 130 may rotate in a first direction. For example, when viewed from the front of the medical device 100 (i.e., the view provided in FIG. 1D), the elongate shaft 130 may rotate in a counterclockwise direction as the second end 124 of the actuator 120 is proximally displaced. Once the actuator 120 has been proximally displaced (see FIGS. 3B and 3C), the practitioner may cause or allow the second end 124 of the actuator 120 to return to a distal position. For example, the practitioner may decrease or remove the proximal force applied to the distal surface 121 of the actuator 120, thereby allowing the biasing member 180 to return the second end 124 of the actuator 120 to a distal position. As the second end 124 of the actuator 120 is distally displaced, the elongate shaft 130 may rotate in a second direction that is opposite of the first direction. Stated differently, the elongate shaft 130 may rotate in a counterclockwise direction when the actuator 120 is proximally displaced and in a clockwise direction as the second end 124 of the actuator 120 is distally displaced (or vice versa).

As the second end 124 of the actuator 120 is displaced relative to the elongate shaft 130, the protrusion 126 of the actuator 120 may be displaced within the slot 111 of the handle 110. For example, as the actuator 120 is displaced relative to the elongate shaft 130, the protrusion 126 of the handle 110 may be displaced vertically within the slot 111.

For example, when the medical device 100 is in the state depicted in FIG. 3A (i.e., the second end 124 of the actuator 120 is disposed adjacent a distal end of the elongate shaft 130), the protrusion 126 may be situated within the slot 111 such that the protrusion 126 is not in contact with either the topmost point nor the bottommost point of the slot 111. In other words, the protrusion 126 may be disposed within a middle portion of the slot 111. As the second end 124 of the actuator 120 is proximally displaced, the second end 124 of the actuator 120 may travel linearly along the elongate shaft 130, initially causing downward displacement of the protrusion 126 within the slot 111 of the handle 110 (see FIG. 3B). As the second end 124 of the actuator 120 is further displaced in a proximal direction, the protrusion 126 may be upwardly displaced within the slot 111 (see FIG. 3C).

In view of the foregoing, one of ordinary skill in the art with the benefit of this disclosure will appreciate that the medical device 100 may be configured for manual, one-handed use in removing, bypassing, or breaking up one or more obstructions within a body lumen. Stated differently, the medical device 100 may be held with a single hand such that the handle 110 is in contact with the palm of the practitioner and the distal surface 121 of the actuator is in contact with one or more fingers of the practitioner. The actuator 120 may then be displaced relative to the elongate shaft 130 to operate the medical device without the assistance of a second hand.

Figure 4A:
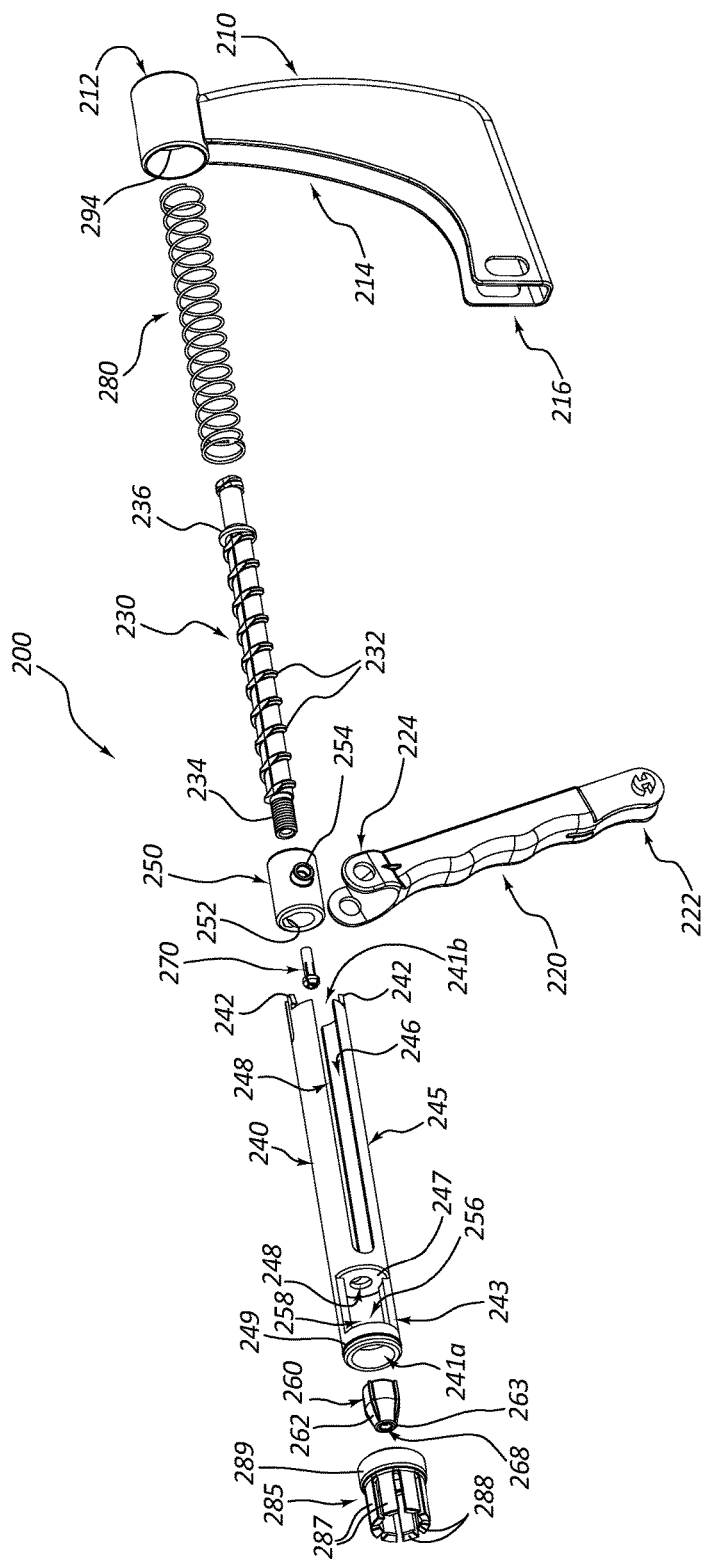
FIG. 4A is an exploded perspective view of another embodiment of a medical device for rotating an elongate medical instrument.
Figure 4B:
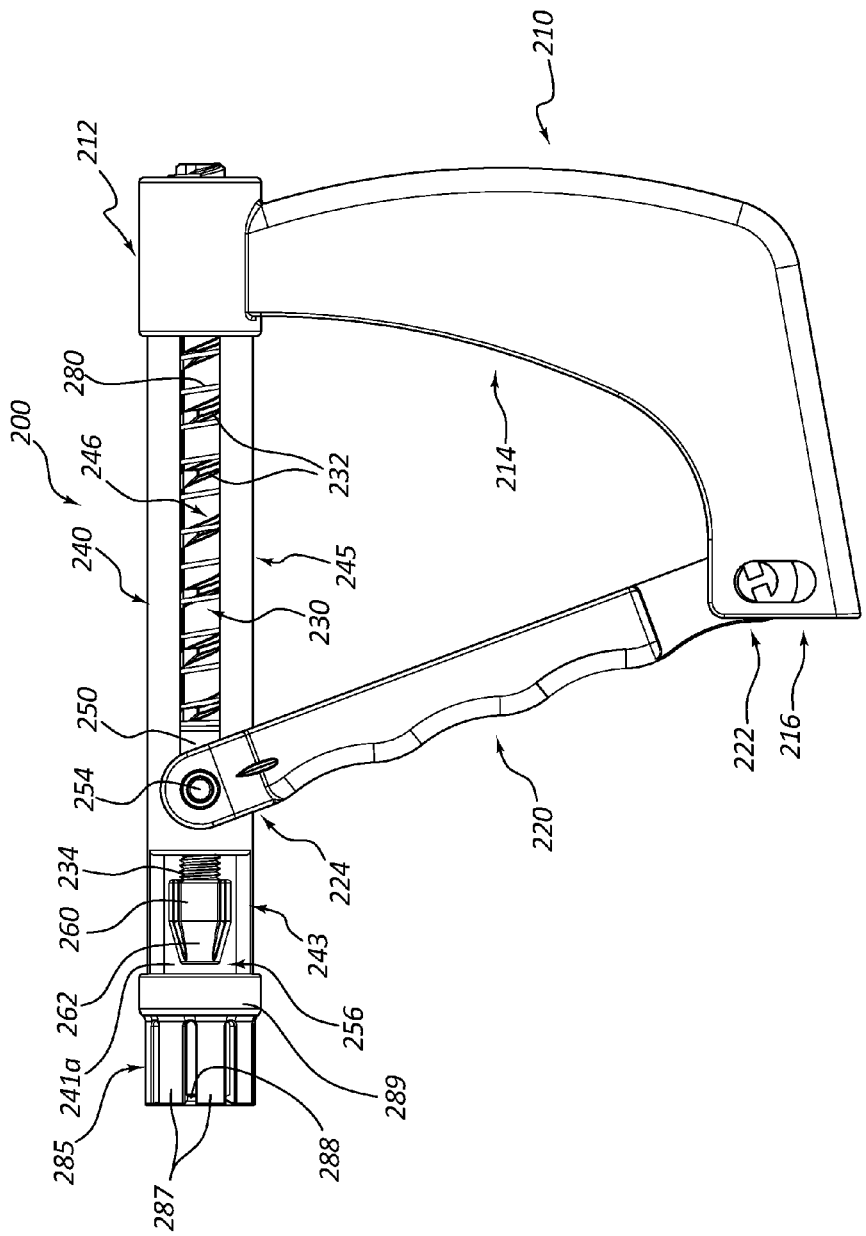
FIG. 4B is a side view of the medical device of FIG. 4A in an assembled configuration.
Figure 4C:
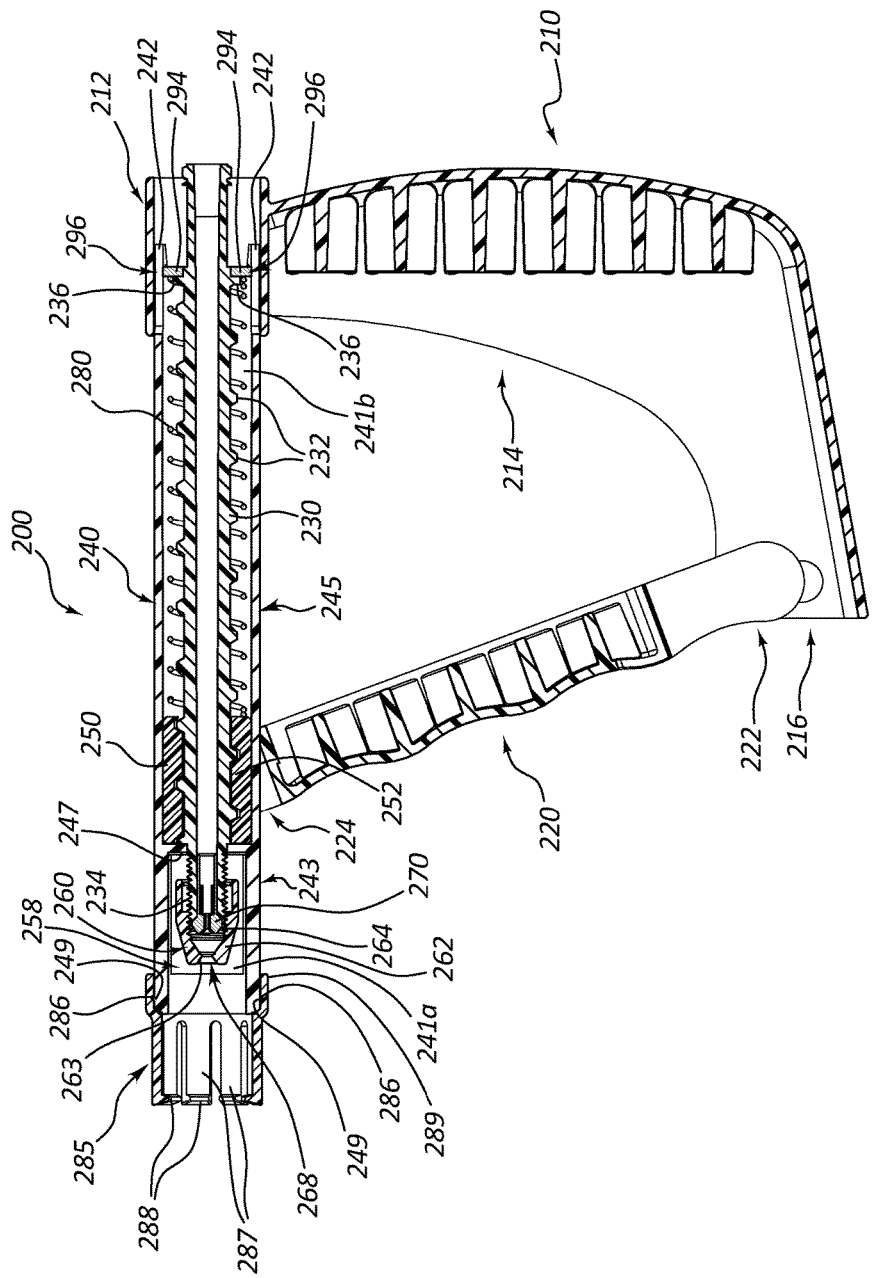
FIG. 4C is a cross-sectional side view of the medical device of FIG. 4A in an assembled configuration.

FIGS. 4A-4C depict an embodiment of a medical device 200 that resembles the medical device 100 described above in certain respects. Accordingly, like features are designated with like reference numerals, with the leading digits incremented to "2." For example, the embodiment depicted in FIGS. 4A-4C includes a handle 210 that may, in some respects, resemble the handle 110 of FIGS. 1A-3C. Relevant disclosure set forth above regarding similarly identified features thus may not be repeated hereafter. Moreover, specific features of the medical device 100 and related components shown in FIGS. 1A-3C may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical device 200 and related components depicted in FIGS. 4A-4C. Any suitable combination of the features, and variations of the same, described with respect to the medical device 100 and related components illustrated in FIGS. 1A-3C can be employed with the medical device 200 and related components of FIGS. 4A-4C, and vice versa. This pattern of disclosure applies equally to further embodiments depicted in subsequent figures and described hereafter, wherein the leading digits may be further incremented.

Figure 5A:
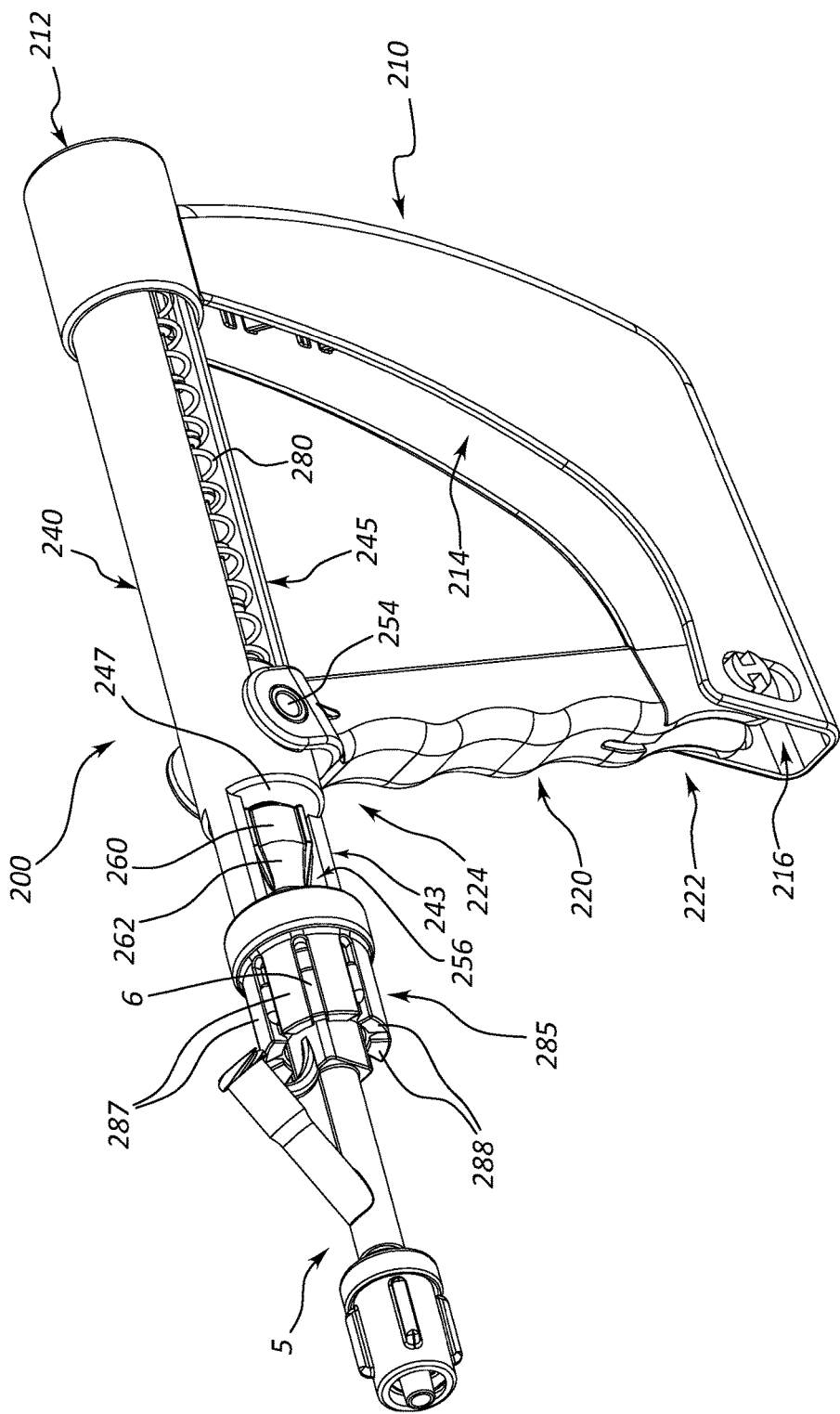
FIG. 5A is a perspective view of the medical device of FIG. 4A coupled to a hemostasis valve.
Figure 5B:
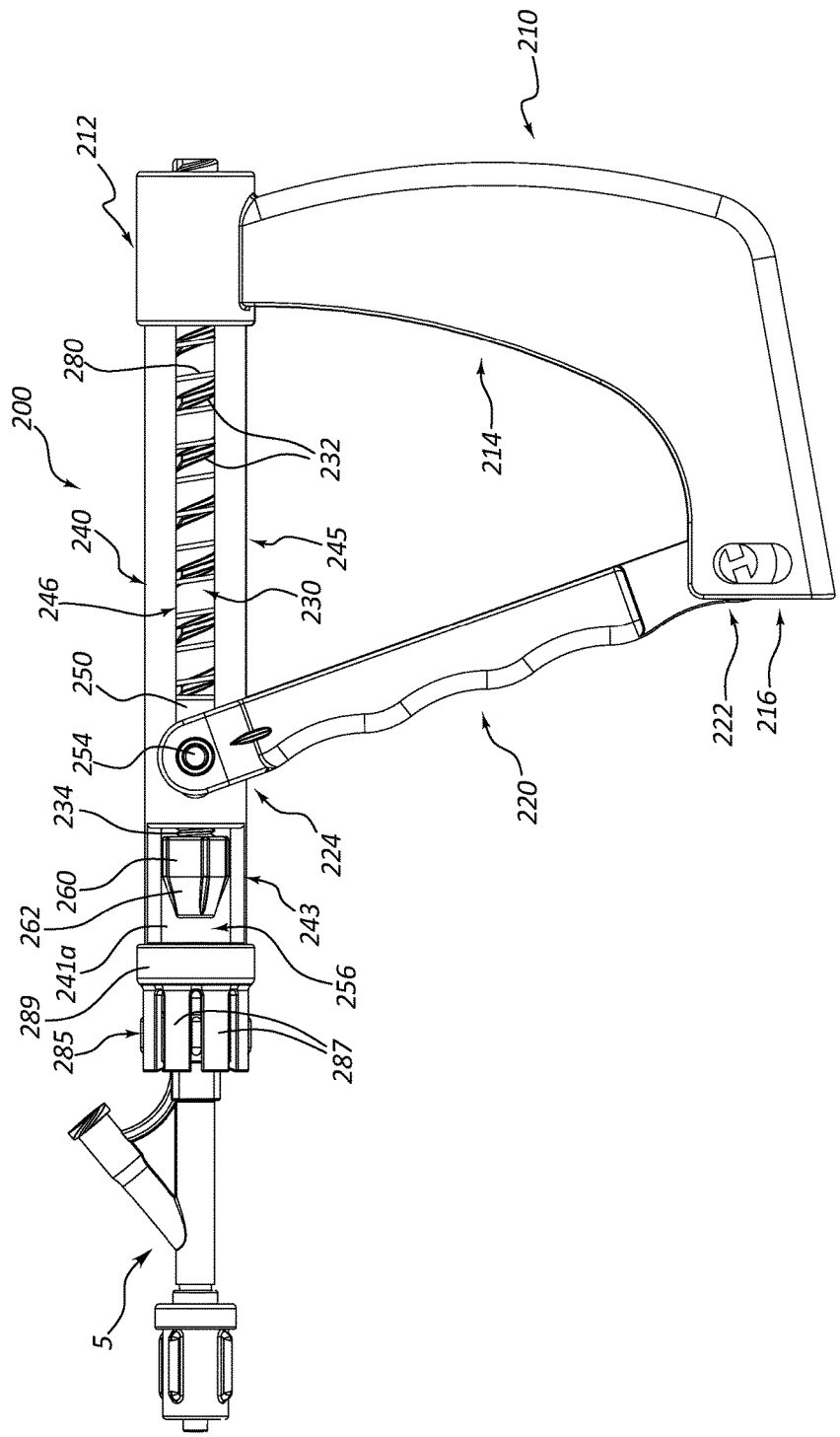
FIG. 5B is a side view of the medical device of FIG. 5A.
Figure 5C:
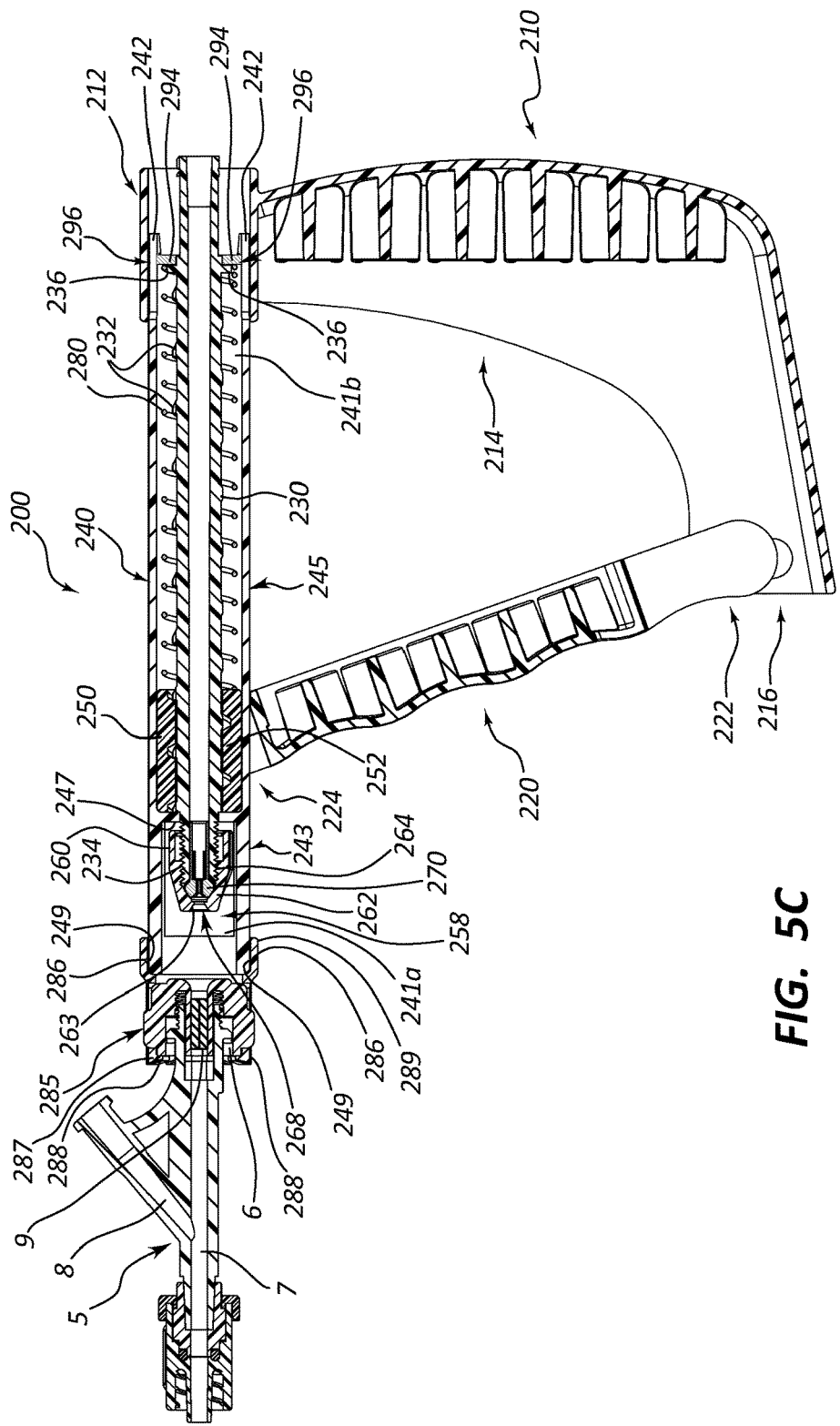
FIG. 5C is a cross-sectional side view of the medical device of FIG. 5A.

FIGS. 4A-4C provide alternative views of a medical device 200 that is configured to rotate an elongate medical instrument. FIGS. 5A-5C provide alternative views of the medical device 200 of FIGS. 4A-4C, wherein the medical device 200 is coupled to a secondary medical device such as hemostasis valve 5. As in FIGS. 1A-1G, the elongate medical instrument is not shown in FIGS. 4A-5C. More particularly, FIG. 4A provides an exploded perspective view of the medical device 200. FIG. 4B provides a side view of the medical device 200 in an assembled configuration. FIG. 4C provides a cross-sectional side view of the assembled medical device 200 in the assembled configuration. FIG. 5A provides a perspective view of the medical device 200 coupled to the hemostasis valve 5 in the assembled configuration. FIG. 5B provides a side view of the medical device 200 coupled to the hemostasis valve 5. FIG. 5C provides a cross-sectional side view of the medical device 200 coupled to the hemostasis valve 5.

Analogous to the medical device 100 of FIGS. 1A-3C, the medical device 200 of FIGS. 4A-5C may also include one or more of the following elements: a handle 210, an actuator 220, an elongate shaft 230, a translatable member 250, a distal endpiece 260, a gripping member 270, and a biasing member 280. The medical device 200 may also include an elongate housing 240 and/or a coupling member 285.

As depicted, the elongate housing 240 can include a distal portion 243 and a proximal portion 245, wherein the distal portion 243 and the proximal portion 245 may be separated by a wall 247 (e.g., an annular wall). The wall 247 can include an opening 248 such that, for example, an elongate medical instrument may be displaced through the elongate housing 240. In some embodiments, the elongate housing 240 may not include a wall 247.

In the assembled configuration (see, e.g., FIGS. 4B and 4C), the distal portion 243 may at least partially surround the endpiece 260 and/or the gripping member 270. Furthermore, in the assembled configuration, the proximal portion 245 may at least partially surround the elongate shaft 230, the translatable member 250, and/or the biasing member 280. The distal portion 243 of the elongate housing 240 may include an inner surface that forms an interior portion 241a that extends through at least a portion of the distal portion 243 of the elongate housing 240. The proximal portion 245 of the elongate housing 240 may also include an inner surface that forms an interior portion 241b that extends through at least a portion of the proximal portion 245 of the elongate housing 240. The interior portion 241a may be sized to accommodate at least a portion of the endpiece 260, the gripping member 270, and/or the elongate shaft 230. The interior portion 241b may be sized to accommodate at least a portion of the elongate shaft 230, the translatable member 250, the gripping member 270, and/or the biasing member 280.

The elongate housing 240 (including the distal portion 243 and the proximal portion 245) may protect the elongate shaft 230, the translatable member 250, the endpiece 260, the gripping member 270, and/or the biasing member 280. For example, the elongate housing 240 may prevent inadvertent contact with the elongate shaft 230, the translatable member 250, the endpiece 260, the gripping member 270, and/or the biasing member 280. In some embodiments, the elongate housing 240 may be coupled to the handle 210 and extend distally from the handle 210. For example, as depicted, the elongate housing 240 can include one or more catches 242 disposed adjacent a proximal end of the elongate housing 240. The one or more catches 242 may be configured to extend through one or more apertures 296 of a surface 294 that extends radially inward from the outer cylindrical surface of an upper portion 212 of the handle 210. As the one or more catches 242 are disposed through the one or more apertures 296, the one or more catches 242 may engage with the surface 294 to securely couple the elongate housing 240 to the handle 210.

In some embodiments, the proximal portion 245 of the elongate housing 240 may include a first slot 246 and a second slot 248 that extend longitudinally along at least a portion of a length of the proximal portion 245 of the elongate housing 240. In some embodiments, the slots 246, 248 are disposed on opposite sides of the proximal portion 245 of the elongate housing 240. The slots 246, 248 may be sized and shaped to accommodate a portion of the translatable member 250, as described above in reference to the medical device 100.

In various embodiments, the distal portion 243 of the elongate housing 240 may include a first opening or first lateral opening 256 and a second opening or second lateral opening 258 that extend longitudinally along at least a portion of a length of the distal portion 243 of the elongate housing 240. In some embodiments, the openings 256, 258 are disposed on opposite sides of the distal portion 243 of the elongate housing 240. The openings 256, 258 may be sized and shaped to provide access to the endpiece 260, for example, such that a practitioner may adjust or rotate the endpiece 260.

As illustrated, the medical device 200 can include a coupling member 285. The coupling member 285 can be coupled to the distal end of the elongate housing 240, for example, when the medical device 200 is in the assembled configuration. Further, the coupling member 285 can extend distally from the distal end and/or the distal portion 243 of the elongate housing 240. In the illustrated embodiment, the coupling member 285 can be coupled to the distal portion 243 of the elongate housing 240 via a snap fit. Specifically, the coupling member 285 can include an annular recess 286 extending along at least a portion of an interior surface of the proximal end of the coupling member 285. Further, an annular ridge 249 can extend along at least a portion of an exterior surface of the distal portion 243 of the elongate housing 240. In the assembled configuration, the annular recess 286 and the annular ridge 249 may engage or snap together to couple the coupling member 285 to the elongate housing 240. In certain other embodiments, the annular recess 286 may be disposed on the elongate housing 240 and the annular ridge 249 may be disposed on the coupling member 285. Other arrangements or configurations of the annular ridge and/or recess are also within the scope of this disclosure. For example, an annular ridge or recess may be disposed on an exterior surface of the coupling member 285 and an annular ridge or recess may be disposed on an interior surface of the elongate housing 240. Other mechanisms for coupling the coupling member 285 to the elongate housing 240 are also within the scope of this disclosure. For example, the coupling member 285 may include one or more threads that are configured to engage with one or more threads disposed on the distal end of the elongate housing 240.

In some embodiments, the coupling member 285 may be configured to be coupled to or selectively coupled to a secondary medical device, such as a hemostasis valve 5 (see FIGS. 5A-5C). Accordingly, the medical device 200 may be coupled to the hemostasis valve 5 via the coupling member 285.

In various embodiments, the coupling member 285 can include a plurality of resilient arms 287, which extend distally from a proximal portion 289 of the coupling member 285. One or more of the resilient arms 287 may further comprise a gripping portion 288. For example, the gripping portion 288 may be disposed at a distal end of the resilient arm 287. The one or more resilient arms 287 and/or the one or more gripping portions 288 can be configured to attach, couple, or connect the medical device 200 to the hemostasis valve 5.

As discussed above, resilient components, such as the one or more resilient arms 287, may have a first shape that can then be elastically deformed or constrained into a second shape but that may return to the first shape when unconstrained. The hemostasis valve 5 can include a shoulder or ridge 6, wherein a portion of the shoulder 6 is configured to engage or interact with the one or more resilient arms 287 and/or the one or more gripping portions 288.

The one or more resilient arms 287, which are unconstrained in the first shape, may be configured to deflect radially outward (i.e., relative to a longitudinal axis of the coupling member 285) into the second shape as the hemostasis valve 5 is disposed or inserted into the coupling member 285. For example, a proximal surface and/or an upper surface of the shoulder 6 of the hemostasis valve 5 may engage with the one or more gripping portions 288 such that the one or more resilient arms 287 transition from the first shape to the second shape. Upon insertion of the hemostasis valve 5 into the coupling member 285, the shoulder 6 can move proximally of the one or more gripping portions 288, and as such, the one or more resilient arms 287 may no longer be deflected outward by an engagement with the proximal and/or upper surfaces of the shoulder 6, such that the one or more resilient arms 287 transition from the second shape to the first shape.

Furthermore, upon coupling of the coupling member 285 to the hemostasis valve 5, the one or more gripping portions 288 may be disposed distally of the shoulder 6 and may be configured to engage a distal surface of the shoulder 6. Such an arrangement of the coupling member 285 and the hemostasis valve 5 and/or the shoulder 6 of the hemostasis valve 5 may couple or secure the hemostasis valve 5 to the coupling member 285 and/or the medical device 200.

The handle 210 may be configured analogously to the handle 110 as described above in reference to the medical device 100. For example, as shown in FIGS. 4A-5C, the handle 210 may include an upper portion 212, an intermediate portion 214, and a lower portion 216. The upper portion 212 of the handle 210 may be coupled to one or more of the elongate housing 240 and the elongate shaft 230.

The actuator 220 may be configured analogously to the actuator 120 as described above in reference to the medical device 100. For example, the actuator 220 may include a first end 222 and a second end 224. As illustrated in FIGS. 4B-5C, the actuator 220 can be coupled to the handle 210 adjacent the first end 222. Further, the actuator 220 may be coupled to the translatable member 250 adjacent the second end 224. Thus, as described above in reference to the medical device 100, the actuator 220 may couple to and extend between the translatable member 250 and the handle 210. As discussed above, displacement of the actuator 220 may cause both displacement of the translatable member 250 along the elongate shaft 230 and rotation of the elongate shaft 230 about its longitudinal axis. In some embodiments, displacement of the actuator 220 causes more linear displacement of the second end 224 of the actuator 220 relative to the handle 210 than linear displacement of the first end 222 of the actuator 220 relative to the handle 210.

The elongate shaft 230 may be configured analogously to the elongate shaft 130 as described above in reference to the medical device 100. For example, the elongate shaft 230 may include one or more sets of threads (e.g., a first set of threads 232 and a second set of threads 234). The first set of threads 232 may be configured for complementary engagement with interior threads 252 of the translatable member 250. Further, in some embodiments, the first set of threads 232 is configured to cause rotation of the elongate shaft 230 in response to displacement of the actuator 220. The second set of threads 234 may be configured for threaded engagement with the endpiece 260.

In some embodiments, the elongate shaft 230 includes one or more annular rings or other protrusions that extend radially outward from the remainder of the elongate shaft 230. For example, an annular ring 236 may be disposed proximal of the first set of threads 232 and be configured for contact with the surface 294 of the upper portion 212 of the housing 240, thereby restricting proximal displacement of the elongate shaft 230 with respect to the handle 210. Distal displacement of the elongate shaft 230 may be restricted by an interaction between the elongate shaft 230 and the wall 247 of the elongate housing 240. For example, in some embodiments, a thread of (or protrusion from) the elongate shaft 230 may interact with an inner surface of the wall 247 of the elongate housing 240 that is disposed between the proximal portion 245 and the distal portion 243 of the elongate housing 240, thereby restricting distal displacement of the elongate shaft 230 relative to the handle 210. In other embodiments, the elongate shaft 230 may include a second annular ring (not shown) that is disposed distal of the first set of threads 232 and proximal of the second set of threads 234. The second annular ring may be configured to interact with the inner surface of the wall 247 of the elongate housing 240 that is disposed between the proximal portion 245 and the distal portion 243 of the elongate housing 240 to restrict distal displacement of the elongate shaft 230 relative to the handle 210. Protrusions other than the annular ring 236 may analogously restrict displacement of the elongate shaft 230 relative to one or more other components of the medical device 200 and are also within the scope of this disclosure.

As discussed above in reference to the medical device 100, the medical device 200 may additionally or alternatively include the translatable member 250. The translatable member 250 may be configured analogously to the translatable member 150. As illustrated, the translatable member 250 may include one or more protrusions 254. The translatable member 250 may be configured to travel longitudinally along the elongate shaft 230, thereby causing rotation of the elongate shaft 230. In the depicted embodiment, as the translatable member 250 travels longitudinally along the elongate shaft 230, the protrusions 254 travel longitudinally within the slots 246, 248 of the proximal portion 245 of the elongate housing 240.

As discussed above in reference to the medical device 100, the medical device 200 may additionally or alternatively include a gripping member or collet 270. In some embodiments, the gripping member 270 is at least partially disposed within a lumen of the elongate shaft 230.

As discussed above in reference to the medical device 100, the medical device 200 may additionally or alternatively include an endpiece 260 that is coupled to the distal end of the elongate shaft 230. The endpiece 260 may include a tapered or frustoconical distal region 262 and a channel that extends through the endpiece 260. Furthermore, a recessed portion 263 that at least partially surrounds an aperture or opening 268 of the channel can be disposed at the distal end of the endpiece 260. The recessed portion 263 may be configured to facilitate insertion of a portion of the elongate medical instrument into a portion of the channel that is proximal of the recessed portion 263. For example, the recessed portion 263 may be sloped toward the aperture 268. The sloped configuration of the recessed portion 263 may facilitate more rapid insertion of a portion of the elongate medical instrument into the medical device 200. The recessed portion 263 may also decrease the dexterity needed (e.g., of a practitioner) for inserting the elongate medical instrument through the aperture 268.

In some embodiments, the endpiece 260 further comprises interior threads 264 that are disposed proximal of the recessed portion 263. The interior threads 264 of the endpiece 260 may be configured for threaded engagement with a distal portion of the elongate shaft 230. For instance, the interior threads 264 of the endpiece 260 may be configured to threadably engage with the second set of threads 234 of the elongate shaft 230.

As discussed above in reference to the medical device 100, in some embodiments, the medical device 200 includes a biasing member 280, such as a spring. The biasing member 280 may be configured analogously to the biasing member 180. The biasing member 280 may distally bias the translatable member 250 and/or the second end 224 of the actuator 220. As described above, the biasing member 280 may be at least partially disposed within the proximal portion 245 of the elongate housing 240 when the medical device 200 is in the assembled configuration.

Figure 6A:
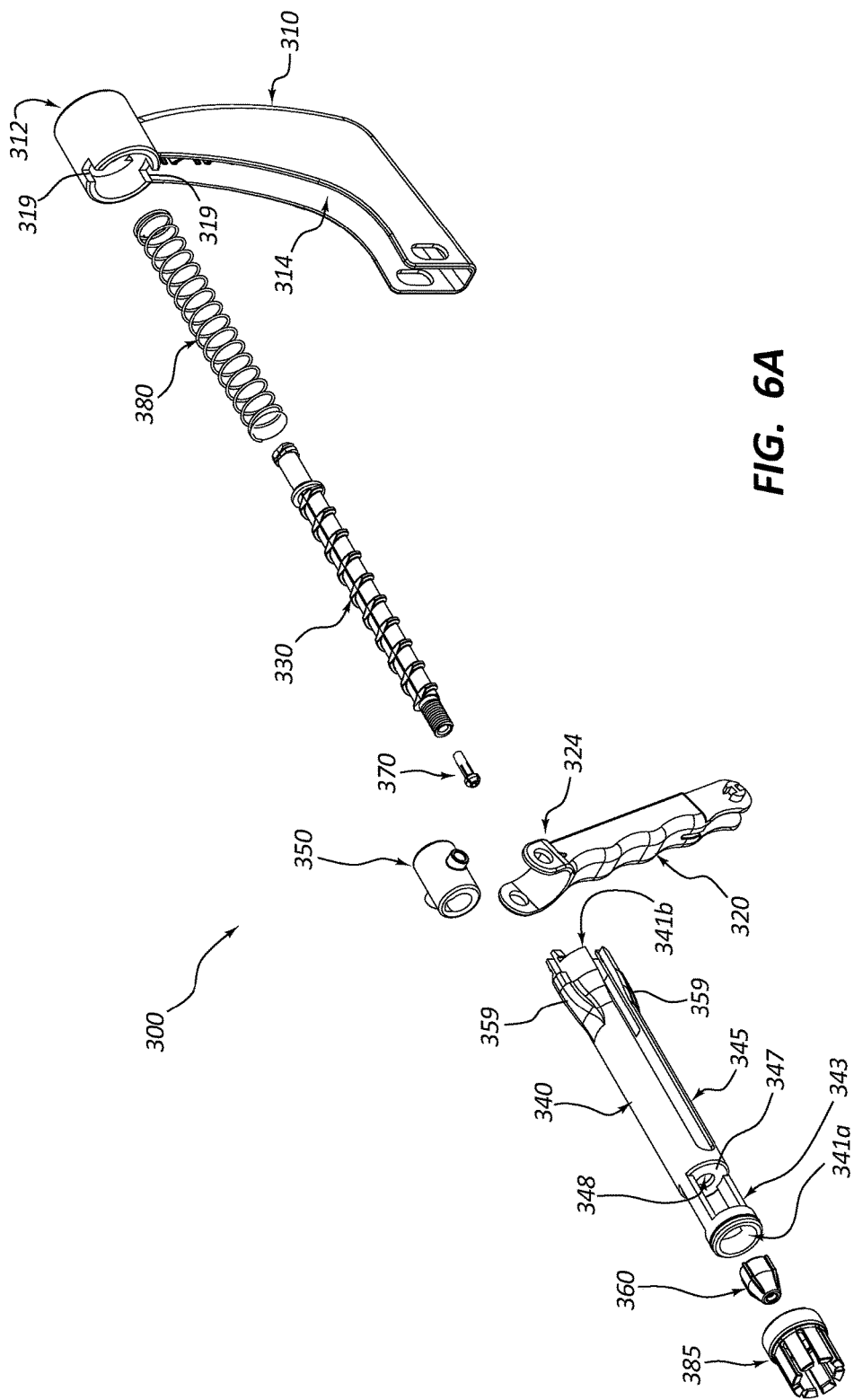
FIG. 6A is an exploded perspective view of another embodiment of a medical device for rotating an elongate medical instrument.
Figure 6B:
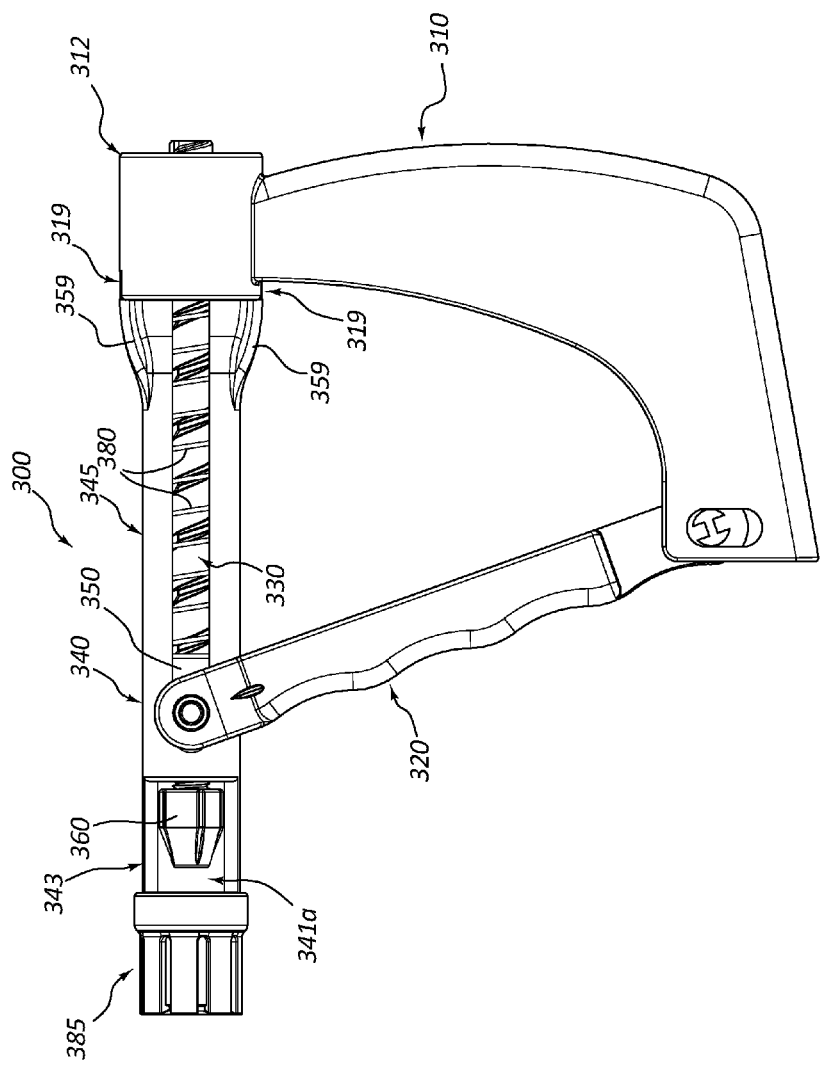
FIG. 6B is a side view of the medical device of FIG. 6A in an assembled configuration.
Figure 6C:
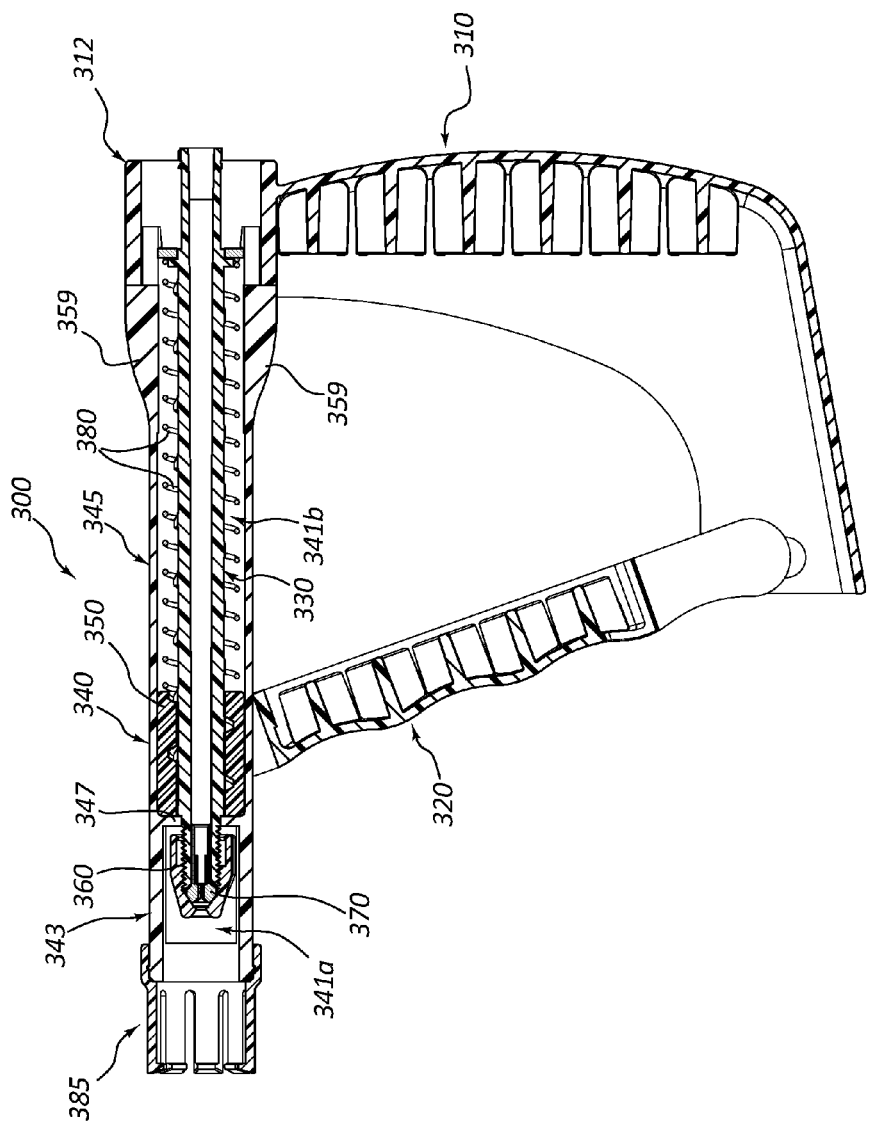
FIG. 6C is a cross-sectional side view of the medical device of FIG. 6A in an assembled configuration.

FIGS. 6A-6C provide alternative views of a medical device 300 that resembles the medical devices 100, 200 described above in certain respects. As noted above, relevant disclosure set forth above regarding similarly identified features of the medical devices 100, 200 may not be repeated in reference to the medical device 300. However, such features may clearly be the same, or substantially the same, as features depicted in other embodiments and/or described with respect to such embodiments. Accordingly, the relevant descriptions of such features apply equally to the features of the medical device 300 and related components depicted in FIGS. 6A-6C. Furthermore, any suitable combination of the features, and variations of the same, described with respect to the medical devices 100, 200 and related components illustrated in FIGS. 1A-5C can be employed with the medical device 300 and related components of FIGS. 6A-6C, and vice versa.

FIG. 6A provides an exploded perspective view of the medical device 300. FIG. 6B provides a side view of the medical device 300 in an assembled configuration. FIG. 6C provides a cross-sectional side view of the assembled medical device 300.

The medical device 300 of FIGS. 6A-6C may also include one or more of the following elements: a handle 310, an actuator 320, an elongate shaft 330, an elongate housing 340, a translatable member 350, a distal endpiece 360, a gripping member 370, a biasing member 380, and a coupling member 385.

As shown, the elongate housing 340 can include a distal portion 343 and a proximal portion 345. The distal portion 343 and the proximal portion 345 can be separated by a wall 347. The wall 347 can include an opening 348 such that, for example, an elongate medical instrument may be displaced through the elongate housing 340. In some embodiments, the elongate housing 340 may not include a wall 347.

In the assembled configuration, the distal portion 343 may at least partially surround the endpiece 360 and/or the gripping member 370. Furthermore, in the assembled configuration, the proximal portion 345 may at least partially surround the elongate shaft 330, the translatable member 350, and/or the biasing member 380. The distal portion 343 of the elongate housing 340 may include an inner surface that forms an interior portion 341a that extends through a portion of the distal portion 343 of the elongate housing 340. The proximal portion 345 of the elongate housing 340 may also include an inner surface that forms an interior portion 341b that extends through the proximal portion 345 of the elongate housing 340. The interior portion 341a may be sized to accommodate at least a portion of the endpiece 360, the gripping member 370, and/or the elongate shaft 330. The interior portion 341b may be sized to accommodate at least a portion of the elongate shaft 330, the translatable member 350, the gripping member 370, and/or the biasing member 380.

The elongate housing 340 may protect the elongate shaft 330, the translatable member 350, the endpiece 360, the gripping member 370, and/or the biasing member 380. For example, the elongate housing 340 may prevent inadvertent contact with the elongate shaft 330, the translatable member 350, the endpiece 360, the gripping member 370, and/or the biasing member 380. In some embodiments, the elongate housing 340 may be coupled to the handle 310 and extend distally from the handle 310.

The elongate housing 340 may further include one or more reinforcement members 359. As depicted, the reinforcement members 359 can be fin-like protrusions or ridges, which extend radially outward in relation to a longitudinal axis of the elongate housing 340. Stated another way, the reinforcement members 359 may extend radially outward from a portion of an outside surface of a portion (e.g., the proximal portion 345) of the elongate housing 340. Further, the handle 310 may include one or more reinforcement member slots 319 (see FIG. 6A). The reinforcement member slots 319 may be configured to receive and/or engage the reinforcement members 359 upon coupling of the elongate house 340 to the handle 310 when the medical device 300 is in the assembled configuration. In the illustrated embodiment, there are two reinforcement members 359 and two corresponding reinforcement member slots 319. The reinforcement members 359 may be disposed on opposite sides of the elongate housing 340. Likewise, the reinforcement member slots 319 may be disposed on opposite sides of an upper portion 312 of the handle 310 such that the reinforcement member slots 319 are arranged to receive and/or engage the reinforcement members 359. In some embodiments, the handle 310 may not include a reinforcement member slot 319. For example, the one or more reinforcement members 359 may abut or be disposed adjacent the upper portion 312 of the handle 310 upon coupling of the elongate housing 340 to the handle 310. In some other embodiments, the medical device 300 may include one, three, four, five, or more reinforcement members 359 and/or reinforcement member slots 319.

The one or more reinforcement members 359 and/or the engagement of the one or more reinforcement members 359 and the reinforcement member slots 319 may strengthen and/or stiffen the elongate housing 340. In certain embodiments, the entire elongate housing 340 is substantially rigid. In various embodiments, a junction of the elongate housing 340 and the handle 310 (due at least in part to the reinforcement member 359 and/or the reinforcement member slots 319) is substantially rigid. Thus, in some embodiments, the elongate housing 340 does not bend, deflect, and/or fail when the medical device 300 is in use. Other shapes, sizes, and configurations of the reinforcement members 359 and/or the reinforcement member slots 319 are also within the scope of this disclosure. For example, the reinforcement members may comprise one or more annular rings that are disposed along a portion of an outside surface of the elongate housing 340. In another example, the reinforcement member slots 319 may include a narrow opening adjacent a distal end of the upper portion 312 of the handle 310 such that a portion of the reinforcement member slot 319 is configured to snap around or engage a portion of the reinforcement member 359 upon coupling of the elongate housing 340 to the handle 310.

Figure 7:
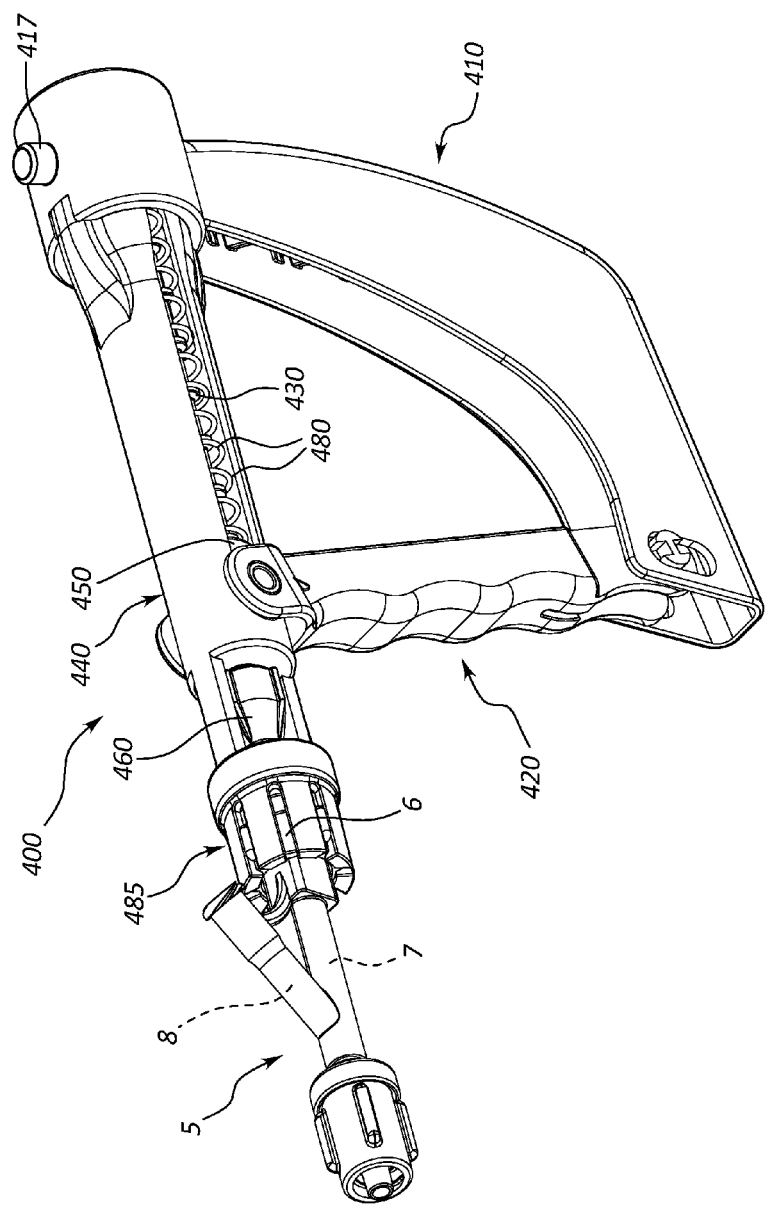
FIG. 7 is a perspective view of another embodiment of a medical device for rotating an elongate instrument coupled to a hemostasis valve.

FIG. 7 is a perspective view of a medical device 400 that resembles the medical devices 100, 200, 300 described above in certain respects. As illustrated, the medical device 400 is coupled to a hemostasis valve 5. The medical device 400 of FIG. 7 may include one or more of the following elements: a handle 410, an actuator 420, an elongate shaft 430, an elongate housing 440, a translatable member 450, a distal endpiece 460, a gripping member (not shown), a biasing member 480, and a coupling member 485. The medical device 400 may also include a second actuator or a tertiary medical device actuator 417. In some embodiments, the second actuator 417 may be configured to activate the hemostasis valve 5 or a tertiary medical device (not shown).

The hemostasis valve 5 can include: a primary lumen 7; a resilient seal 9 disposed in the primary lumen 7 (see FIG. 5C); and a secondary lumen 8 that branches from the primary lumen 7 at a position distal of the resilient seal 9. An elongate medical instrument, as discussed above, can pass through each of the primary lumen 7 and the resilient seal 9. The resilient seal 9 can be configured to form a seal around the elongate medical instrument as the elongate medical instrument passes through the resilient seal 9 and/or when the elongate medical instrument is disposed in the resilient seal 9.

In some embodiments, the hemostasis valve 5 may be coupled to a tertiary medical device such as, but not limited to, a vacuum source. The term "vacuum source," as used herein, is broad enough to include any negative gauge pressure source. For example, a vacuum source includes, but is not limited to, a suction line, a vacuum line, a syringe having negative gauge pressure in a reservoir, and so on. The vacuum source may be coupled to the secondary lumen 8 of the hemostasis valve 5. In certain embodiments, the vacuum source can provide suction through the secondary lumen 8 and the primary lumen 7. A catheter (not shown) may be coupled to and extend distally from a distal end of the hemostasis valve 5. The elongate medical instrument, which passes through the hemostasis valve 5, can further pass through the catheter.

In some embodiments, the second actuator 417 may be configured to activate the tertiary medical device during use of the medical device 400. For example, a practitioner may engage the second actuator 417 to activate a vacuum source. Activation of the vacuum source can form suction that extends through the catheter (e.g., the catheter in which the elongate medical instrument passes). The suction may be used to remove debris or pieces of an obstruction from the blood stream of a patient that may be dislodged or generated during use of the medical device 400 and/or the elongate medical instrument in a medical procedure as described herein. In various embodiments, the vacuum source may include a syringe having negative gauge pressure in a reservoir. In such embodiments, a practitioner may suction debris into the reservoir, the debris may be collected, and the collected debris may be analyzed.

In certain embodiments, a practitioner may engage the second actuator 417 to activate an actuatable seal (not shown) that is disposed in the secondary lumen 8. The actuatable seal may be configured to transition between an open configuration and a closed configuration. In the open configuration, the actuatable seal may allow or permit suction that is formed by a vacuum source, which is coupled to the secondary lumen 8, to pass through each of the secondary lumen 8, the primary lumen 7, and/or a catheter that is coupled to the distal end of the hemostasis valve 5. In the closed configuration, the actuatable seal may limit or prevent suction formed by the vacuum source from passing through each of the secondary lumen 8, the primary lumen 7, and/or the catheter.

Each of the medical devices 200, 300, 400 may operate in an analogous manner to that of the medical device 100. Accordingly, the descriptions above in reference to FIGS. 2A-3C can be adapted for use with the medical devices 200, 300, 400.

Additionally, methods for disrupting or bypassing an obstruction within a lumen may include obtaining a medical device such as the medical devices 100, 200, 300, 400. The medical device can include one or more of a rotatable shaft (e.g., the elongate shaft 130, 230, 330, 430), an endpiece that is disposed adjacent a distal end of the rotatable shaft, an elongate housing that is at least partially disposed around each of the rotatable shaft and the endpiece, a coupling member that extends distally from the elongate housing, and/or an actuator. The methods can further include coupling a hemostasis valve (or another suitable secondary medical device) to the medical device via the coupling member. The methods can also include obtaining an elongate medical instrument and inserting a portion of the elongate medical instrument into an aperture of the hemostasis valve and an aperture of the medical device that is disposed in the endpiece. Furthermore, the methods may include engaging the elongate medical instrument such that the elongate medical instrument is coupled to the rotatable shaft.

The elongate medical instrument may then be inserted into a lumen (e.g., a vascular lumen) in which there is an obstruction. The actuator of the medical device can then be displaced, wherein the displacement of the actuator causes rotation of the elongate medical instrument within the lumen.

In some embodiments, the methods may further include one or more of advancing and retracting the elongate medical instrument within the lumen while displacing the actuator. Furthermore, a second actuator may be activated or engaged (e.g., by a practitioner) such that the secondary medical device (or a tertiary medical device that is coupled to the secondary medical device) is activated. In some embodiments, a vacuum source that is coupled to the hemostasis valve may be activated by the second actuator such that a practitioner may remove one or more pieces of debris that may be dislodged into the vascular lumen during the disruption of the obstruction in the lumen.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A medical device comprising:
   a handle;
   an elongate shaft extending distally from the handle, the elongate shaft comprising a plurality of threads;
   a translatable member in threaded engagement with the plurality of threads of the elongate shaft;
   a gripping member coupled to the elongate shaft, wherein the gripping member is configured to selectively couple to an elongate medical instrument;
   an endpiece disposed adjacent a distal end of the elongate shaft;
   an elongate housing coupled to and extending distally from the handle, the elongate housing including a distal portion and a proximal portion, the distal portion at least partially surrounding the endpiece, and the proximal portion at least partially surrounding the elongate shaft;
   a coupling member coupled to and extending distally from the distal portion of the elongate housing, the coupling member configured to selectively couple the medical device to a secondary medical device; and
   an actuator coupled to the translatable member, wherein displacement of the actuator causes both displacement of the translatable member along the elongate shaft and rotation of the elongate shaft,
   wherein the endpiece and the elongate shaft are configured to threadably engage with one another, and wherein the endpiece is configured to interact with the gripping member such that the gripping member is in a contracted state when the endpiece is in full threaded engagement with the elongate shaft.

2. The medical device of claim 1, the proximal portion of the elongate housing comprising an inner surface defining an interior portion and at least one slot that extends longitudinally along a length of the elongate housing; and
   the distal portion of the elongate housing comprising at least one lateral opening.

3. The medical device of claim 1, further comprising the secondary medical device, wherein the secondary medical device is a hemostasis valve, and wherein the hemostasis valve is coupled to the coupling member.

4. The medical device of claim 3, the handle comprising a medical device actuator configured to activate at least one of the secondary medical device or a tertiary medical device.

5. The medical device of claim 1, further comprising a biasing member that is at least partially disposed within the proximal portion of the elongate housing, wherein the biasing member distally biases at least a portion of the actuator.

6. The medical device of claim 1, wherein the actuator comprises a first end and a second end, wherein the actuator is coupled to the handle adjacent the first end and to the translatable member adjacent the second end.

7. The medical device of claim 6, wherein the handle is directly coupled to the actuator and a bottom surface of the handle is not displaced toward or away from the elongate shaft when the actuator is displaced toward the handle.

8. A medical device comprising:
   a handle;
   an elongate shaft extending distally from the handle, the elongate shaft comprising a plurality of threads;
   a translatable member comprising an interior surface configured for threaded engagement with the plurality of threads of the elongate shaft;
   a collet coupled to the elongate shaft, the collet configured to be coupled to an elongate medical instrument;
   an actuator comprising a first end and a second end, wherein the actuator is directly coupled to the handle adjacent the first end and coupled to the translatable member adjacent the second end, wherein displacement of the actuator causes both displacement of the translatable member along the elongate shaft and rotation of the elongate shaft, and wherein a bottom surface of the handle is not displaced toward the elongate shaft when the actuator is displaced toward the handle;
   an elongate housing coupled to the handle, the elongate housing at least partially disposed around each of the collet and the elongate shaft, the elongate housing comprising:
      a proximal portion comprising a reinforcement member extending radially outward from a portion of an outside surface of the proximal portion, the proximal portion at least partially disposed around the elongate shaft; and
      a distal portion at least partially disposed around an endpiece coupled to the collet; and
   a coupling member coupled to a distal end of the elongate housing.

9. The medical device of claim 8, further comprising an endpiece coupled to the collet, the endpiece comprising a recessed portion at least partially surrounding an opening for guiding disposition of a portion of the elongate medical instrument to the collet.

10. The medical device of claim 8, the proximal portion further comprising:
    an inner surface defining an interior portion; and
    at least one slot that extends longitudinally along a length of the proximal portion, the at least one slot configured to receive at least a portion of the translatable member.

11. The medical device of claim 10, wherein the handle comprises an elongate slot that is configured to receive a protrusion from the actuator, wherein displacement of the actuator causes displacement of the protrusion within the elongate slot, and wherein the medical device is configured such that displacement of the protrusion within the elongate slot comprises displacement of the protrusion in a vertical direction.

12. The medical device of claim 11, wherein the medical device is configured such that displacement of the actuator from a distal position to a proximal position initially causes downward displacement of the protrusion relative to the slot and subsequently causes upward displacement of the protrusion relative to the slot.

13. The medical device of claim 8, wherein the medical device is configured such that displacement of the actuator causes linear displacement of the translatable member.

14. A medical device comprising:
- a handle;
- an elongate shaft extending distally from the handle, the elongate shaft comprising a plurality of threads;
- a translatable member in threaded engagement with the plurality of threads of the elongate shaft;
- a gripping member coupled to the elongate shaft, wherein the gripping member is configured to selectively couple to an elongate medical instrument;
- an endpiece disposed adjacent a distal end of the elongate shaft;
- an elongate housing coupled to and extending distally from the handle, the elongate housing including a distal portion and a proximal portion, the distal portion at least partially surrounding the endpiece, and the proximal portion at least partially surrounding the elongate shaft;
- a secondary medical device, wherein the secondary medical device is a hemostasis valve, and wherein the hemostasis valve is coupled to a coupling member;
- wherein the coupling member is coupled to and extending distally from the distal portion of the elongate housing, the coupling member configured to selectively couple the medical device to the secondary medical device; and
- an actuator coupled to the translatable member, wherein displacement of the actuator causes both displacement of the translatable member along the elongate shaft and rotation of the elongate shaft,
- wherein the distal portion of the elongate housing comprises at least one lateral opening that enables access to the endpiece.

* * * * *